(12) United States Patent
Abouabdellah et al.

(10) Patent No.: US 8,912,218 B2
(45) Date of Patent: Dec. 16, 2014

(54) ALKYLTHIAZOL CARBAMATE DERIVATIVES, PREPARATION THEREOF AND THERAPEUTIC USE THEREOF

(75) Inventors: Ahmed Abouabdellah, Paris (FR); Jochen Görlitzer, Frankfurt am Main (DE); Peter Hamley, Frankfurt am Main (DE); Antoine Ravet, Paris (FR)

(73) Assignee: Sanofi, Paris (FR)

( * ) Notice: Subject to any disclaimer, the term of this patent is extended or adjusted under 35 U.S.C. 154(b) by 362 days.

(21) Appl. No.: 13/003,713

(22) PCT Filed: Jul. 21, 2009

(86) PCT No.: PCT/FR2009/051457
§ 371 (c)(1),
(2), (4) Date: May 19, 2011

(87) PCT Pub. No.: WO2010/010288
PCT Pub. Date: Jan. 28, 2010

(65) Prior Publication Data
US 2011/0212963 A1    Sep. 1, 2011

(30) Foreign Application Priority Data
Jul. 23, 2008  (FR) ...................................... 08 04179

(51) Int. Cl.
C07D 401/04      (2006.01)
C07D 417/14      (2006.01)

(52) U.S. Cl.
CPC .................................... C07D 417/14 (2013.01)
USPC ........... 514/318; 514/313; 514/333; 544/333; 546/193; 546/194

(58) Field of Classification Search
CPC . A61K 31/4545; C07D 401/04; C07D 401/14
USPC .......... 514/318, 313, 333; 546/193, 194, 159; 544/333
See application file for complete search history.

(56) References Cited

U.S. PATENT DOCUMENTS

| 7,691,841 B2 * | 4/2010 | Legrand .................... 514/210.01 |
| 7,902,367 B2 * | 3/2011 | Nomura et al. ................ 546/209 |
| 8,293,752 B2 * | 10/2012 | Chen et al. ..................... 514/256 |
| 2012/0015950 A1 * | 1/2012 | Abouabdellah et al. ....... 514/249 |

FOREIGN PATENT DOCUMENTS

| EP | 1 780 210 A1 | 5/2007 |
| FR | 2 854 633 | 11/2004 |

OTHER PUBLICATIONS

Ahn et al. "Fatty acid amide . . . " Exp. Opin. Drug Dsicov. 4(7)763-784 (2009).*
Ahn et al. (2) "Discovery and character . . . " Chem. Biol. 16(4) 411-420 (2009).*
Improper Marlush p. 1, 64-67 (2011).*
Nomura et al. "Prepartion of cyclic . . . " CA144:233066 (2006).*
Patani et al. "Bioisosterism . . . " Chem. Rev. 96 p. 3147-3176 (1996).*
Jordan "Tamoxifen . . . " Nature Rev. p. 208-213 (2003).*
Dorwald "side reactions . . . " p.ix (2005).*
"New matter" USPTO newletter vol. 2 (1) p. 1-2 (2005).*
International Search Report dated Jan. 20, 2010.

* cited by examiner

*Primary Examiner* — Celia Chang
(74) *Attorney, Agent, or Firm* — Scully, Scott, Murphy & Presser P.C.

(57) ABSTRACT

The invention relates to the novel products of formula (I): in which: Ra represents H, Hal, aryl or heteroaryl, which is optionally substituted; Rb represents H, Rc, —COORc-CO—Rc or —CO—NRcRd; where Rc represents alkyl, cycloalkyl, heterocycloalkyl, aryl and heteroaryl, all optionally substituted; Rd represents H, alk or cycloalkyl; these products being in all the isomer forms and the salts, as medicaments, in particular as MET inhibitors.

11 Claims, No Drawings

ALKYLTHIAZOL CARBAMATE DERIVATIVES, PREPARATION THEREOF AND THERAPEUTIC USE THEREOF

The invention relates to alkylthiazole carbamate derivatives, their preparation and their application in therapy.

There is still a need to find and to develop products which are inhibitors of the enzyme FAAH. The compounds of the invention meet this objective.

The compounds of the invention are of the general formula (I):

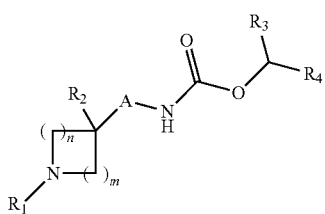

in which
$R_2$ represents a hydrogen or fluorine atom, a hydroxyl, cyano, trifluoromethyl, $C_{1-6}$ alkyl or $C_{1-6}$ alkoxy group or a group $NR_8R_9$;
n represents an integer 1, 2 or 3 and m represents an integer 1 or 2;
A represents a covalent bond or a $C_{1-8}$ alkylene group;
$R_1$ represents A group $R_5$ which is optionally substituted by one or more groups $R_6$ and/or $R_7$;
  $R_5$ represents a group selected from a phenyl, pyridinyl, pyridazinyl, pyrimidinyl, pyrazinyl, triazinyl, naphthalenyl, quinolinyl, isoquinolinyl, phthalazinyl, quinazolinyl, quinoxalinyl, cinnolinyl or naphthyridinyl;
  $R_6$ represents a halogen atom, a cyano, —$CH_2CN$, nitro, hydroxyl, $C_{1-6}$ alkyl, $C_{1-6}$ alkoxy, $C_{1-8}$ thioalkyl, $C_{1-8}$ haloalkyl, $C_{1-8}$ haloalkoxy, $C_{1-6}$ halothioalkyl, $C_{3-7}$ cycloalkyl, $C_{3-7}$ cycloalkyl-$C_{1-3}$ alkylene or $C_{3-7}$ cycloalkyl-$C_{1-3}$ alkylene-O— group, or a group $NR_8R_9$, $NR_8COR_9$, $NR_8CO_2R_9$, $NR_8SO_2R_9$, $NR_8SO_2NR_8R_9$, $COR_8$, $CO_2R_8$, $CONR_8R_9$, $SO_2R_8$, $SO_2NR_8R_9$ or —O—($C_{1-3}$-alkylene)-O—;
  $R_7$ represents a group selected from a furanyl, pyrrolyl, thienyl, oxazolyl, isoxazolyl, thiazolyl, isothiazolyl, imidazolyl, pyrazolyl, oxadiazole, thiadiazole, phenyl, pyridinyl, pyridazinyl, pyrimidinyl, pyrazinyl, triazine, naphthalenyl, quinolinyl, isoquinolinyl, phthalazinyl, quinazolinyl, quinoxalinyl, cinnolinyl, naphthyridinyl, imidazopyrimidinyl, thienopyrimidinyl, benzofuranyl, benzothienyl, benzimidazolyl, benzoxazolyl, benzisoxazolyl, benzothiazolyl, benzisothiazolyl, indolyl, isoindolyl, indazolyl, pyrrolopyridinyl, furopyridinyl, thienopyridinyl, imidazopyridinyl, pyrazolopyridinyl, oxazolopyridinyl, isoxazolopyridinyl, thiazolopyridinyl, phenyloxy, benzyloxy or pyrimidinoxy, the group or groups $R_7$ being able to be substituted by one or more groups $R_6$ which are identical or different from one another;
$R_3$ represents a hydrogen or fluorine atom, a $C_{1-6}$ alkyl group or a trifluoromethyl group;
$R_4$ represents a thiazole which is optionally substituted by one or more substituents selected from a halogen atom, a $C_{1-6}$ alkyl, $C_{1-6}$ haloalkyl, $C_{3-7}$ cycloalkyl, $C_{3-7}$ cycloalkyl-$C_{1-3}$ alkylene, $C_{1-8}$ haloalkoxy, cyano, $NR_8R_9$, $NR_8COR_9$, $NR_8CO_2R_9$, $NR_8SO_2R_9$, $NR_8SO_2NR_8R_9$, $COR_8$, $CO_2R_8$, $CONR_8R_9$, $SO_2R_8$, $SO_2NR_8R_9$, —O—($C_{1-3}$-alkylene)-O—, phenyl, phenyloxy, benzyloxy, pyridinyl, pyrazinyl, pyridazinyl, triazinyl or pyrimidinyl group, it being possible for the phenyl, phenyloxy, pyridinyl, pyrazinyl, pyridazinyl, triazinyl and pyrimidinyl groups to be substituted by one or more substituents selected from a halogen atom and a cyano, nitro, $C_{1-6}$ alkyl, $C_{1-6}$ alkoxy, $C_{1-6}$ thioalkyl, $C_{1-8}$ haloalkyl, $C_{1-6}$ haloalkoxy, $C_{1-6}$ halothioalkyl, $C_{3-7}$ cycloalkyl, $C_{3-7}$ cycloalkyl-$C_{1-3}$ alkylene group;
$R_8$ and $R_9$ represent independently of one another a hydrogen atom or a $C_{1-8}$ alkyl group,
or form, with the atom or atoms bearing them,
in the case of $NR_8R_9$, a ring selected from azetidine, pyrrolidine, piperidine, morpholine, thiomorpholine, azepine, oxazepine or piperazine ring, this ring being optionally substituted by a $C_{1-6}$ alkyl or benzyl group;
in the case of $NR_8COR_9$, a lactam ring; in the case of $NR_8CO_2R_9$, an oxazolidinone, oxazinone or oxazepinone ring; in the case of $NR_8SO_2R_9$, a sultam ring; in the case of $NR_8SO_2NR_8R_9$, a thiazolidine dioxide or thiadiazinane dioxide ring.

The following compounds, described in document EP1780210, are excluded from the general formula (I):
methyl 2-(3-{[2-(4-chlorophenyl)-4-methylthiazol-5-yl]methoxycarbonylamino}piperidin-1-yl)benzoate;
2-(3-{[2-(4-chlorophenyl)-4-methylthiazol-5-yl]methoxycarbonylamino}piperidin-1-yl)benzoic acid;
methyl 3-(3-{[2-(4-chlorophenyl)-4-methylthiazol-5-yl]methoxycarbonylamino}piperidin-1-yl)benzoate;
3-(3-{[2-(4-chlorophenyl)-4-methylthiazol-5-yl]methoxycarbonylamino}piperidin-1-yl)benzoic acid.

Among the compounds of general formula (I) a first subgroup of compounds is composed of the compounds for which $R_2$ represents a hydrogen atom.

Among the compounds of general formula (I) a second subgroup of compounds is composed of the compounds for which n represents an integer 1 or 2 and m represents an integer 2.

Among the compounds of general formula (I) a third subgroup of compounds is composed of the compounds for which A represents a $C_{1-8}$ alkylene group, more particularly a methylene or ethylene group.

Among the compounds of general formula (I), a fourth subgroup of compounds is composed of the compounds for which $R_1$ represents group $R_5$ which is optionally substituted by one or more groups $R_6$ and/or $R_7$;
  $R_5$ represents a pyridinyl or quinolinyl group;
  $R_6$ represents a halogen atom, more particularly a chlorine or fluorine atom, a cyano, —$CH_2CN$, $C_{1-6}$ alkyl, more particularly methyl, isopropyl or isobutyl, $C_{1-6}$ alkoxy, more particularly methoxy or ethoxy, $C_{1-6}$ haloalkyl, more particularly trifluoromethyl, $C_{3-7}$ cycloalkyl, more particularly cyclohexyl, or $C_{3-7}$ cycloalkyl-$C_{1-3}$ alkylene-O—, more particularly cyclopropyl-$CH_2$—O— group, or a group $NR_8R_9$, $NR_8COR_9$, $NR_8CO_2R_9$, $NR_8SO_2R_9$, $CONR_8R_9$, $SO_2R_8$ or $SO_2NR_8R_9$;
  $R_7$ represents a group selected from a thienyl, isoxazolyl, pyrazolyl, phenyl, pyridinyl, pyrimidinyl, naphthalenyl, quinolinyl or isoquinolinyl, it being possible for the group or groups $R_7$ to be substituted by one or more groups $R_6$ which are identical or different from one another;
  $R_8$ and $R_9$ represent independently of one another a hydrogen atom or a $C_{1-6}$ alkyl, more particularly methyl, ethyl, propyl or tert-butyl group, or form with the atom or atoms bearing them a ring selected from pyrrolidine, piperidine and morpholine rings.

Among the compounds of general formula (I) a fifth subgroup of compounds is composed of the compounds for which $R_3$ represents a hydrogen atom, a $C_{1-6}$ alkyl group, more particularly methyl, or a trifluoromethyl group.

Among the compounds of general formula (I) a sixth subgroup of compounds is composed of the compounds for which $R_4$ represents a thiazole which is optionally substituted by one or more substituents selected from a halogen atom, more particularly chlorine, a $C_{1-6}$ alkyl group, more particularly methyl, a $C_{1-6}$ haloalkyl group, more particularly trifluoromethyl, a pyridinyl group or a group $CONR_8R_9$;
$R_8$ and $R_9$ represent independently of one another a hydrogen atom or a $C_{1-6}$ alkyl group, more particularly a methyl.

Among the compounds of general formula (I) a seventh subgroup of compounds is composed of the compounds of general formula (I) in which at one and the same time $R_1$ and/or $R_2$ and/or $R_3$ and/or $R_4$ and/or n and/or m and/or A are as defined in the groups above.

The compounds of general formula (I) include the following compounds (IUPAC nomenclature generated by the AutoNom software):

1. thiazol-4-ylmethyl 6'-[thiophen-3-yl-3,4,5,6-tetrahydro-2H-[1,2']bipyridinyl-4-yl]methylcarbamate
2. thiazol-4-ylmethyl 2-[(6'-thiophen-3-yl-3,4,5,6-tetrahydro-2H-[1,2']bipyridinyl-4-yl]ethylcarbamate
3. thiazol-4-ylmethyl 6'-[(4-methylthiophen-3-yl)-3,4,5,6-tetrahydro-2H-[1,2']bipyridinyl-4-yl]methylcarbamate
4. thiazol-4-ylmethyl 2-[6'-(4-methylthiophen-3-yl)-3,4,5,6-tetrahydro-2H-[1,2']bipyridinyl-4-yl]ethylcarbamate
5. thiazol-4-ylmethyl 2-[6'-(5-cyanothiophen-2-O-3,4,5,6-tetrahydro-2H-[1,2']bipyridinyl-4-yl]ethylcarbamate
6. thiazol-2-ylmethyl 2-[6'-(2-methyl-2H-pyrazol-3-yl)-3,4,5,6-tetrahydro-2H-[1,2']bipyridinyl-4-yl]ethylcarbamate
7. thiazol-4-ylmethyl 6'-[2-methyl-2H-pyrazol-3-yl)-3,4,5,6-tetrahydro-2H-[1,2']bipyridinyl-4-yl]methylcarbamate
8. thiazol-4-ylmethyl 2-[6'-(2-methyl-2H-pyrazol-3-yl)-3,4,5,6-tetrahydro-2H-[1,2']bipyridinyl-4-yl]ethylcarbamate
9. thiazol-2-ylmethyl 2-[6'-(1-methyl-1H-pyrazol-4-yl)-3,4,5,6-tetrahydro-2H-[1,21']bipyridinyl-4-yl]ethylcarbamate
10. thiazol-4-ylmethyl 2-[6'-(1-methyl-1H-pyrazol-4-yl)-3,4,5,6-tetrahydro-2H-[1,2']bipyridinyl-4-yl]ethylcarbamate
11. thiazol-4-ylmethyl 2-[5'-(1-methyl-1H-pyrazol-4-yl)-3,4,5,6-tetrahydro-2H-[1,2']bipyridinyl-4-yl]ethylcarbamate
12. thiazol-4-ylmethyl 2-[5'-(2-methyl-2H-pyrazol-3-yl)-3,4,5,6-tetrahydro-2H-[1,2']bipyridinyl-4-yl]ethylcarbamate
13. thiazol-2-ylmethyl 2-[6'-(1-isobutyl-1H-pyrazol-4-yl)-3,4,5,6-tetrahydro-2H-[1,2']bipyridinyl-4-yl]ethylcarbamate
14. thiazol-4-ylmethyl 6'-[(1-isobutyl-1H-pyrazol-4-O-3,4,5,6-tetrahydro-2H-[1,2]bipyridinyl-4-yl]methylcarbamate
15. thiazol-4-ylmethyl 2-[6'-(1-isobutyl-1H-pyrazol-4-yl)-3,4,5,6-tetrahydro-2H-[1,2']bipyridinyl-4-yl]ethylcarbamate
16. thiazol-4-ylmethyl 2-[5'-(1-isobutyl-1H-pyrazol-4-yl)-3,4,5,6-tetrahydro-2H-[1,2]bipyridinyl-4-yl]ethylcarbamate
17. thiazol-4-ylmethyl 6'-[(3,5-dimethylisoxazol-4-yl)-3,4,5,6-tetrahydro-2H-[1,2']bipyridinyl-4-yl]methylcarbamate
18. thiazol-4-ylmethyl 2-[6'-(3,5-dimethylisoxazol-4-yl)-3,4,5,6-tetrahydro-2H-[1,2']bipyridinyl-4-yl]ethylcarbamate
19. thiazol-4-ylmethyl (4"-methoxy-3,4,5,6-tetrahydro-2H-[1,2'; 6',3"]terpyridin-4-yl)methylcarbamate
20. thiazol-4-ylmethyl 2-(4"-methoxy-3,4,5,6-tetrahydro-2H-[1,2'; 6',3"]terpyridin-4-yl)ethylcarbamate
21. thiazol-2-ylmethyl 2-(5"-fluoro-3,4,5,6-tetrahydro-2H-[1,2'; 6',3"]terpyridin-4-yl)ethylcarbamate
22. thiazol-4-ylmethyl 2-(5"-fluoro-3,4,5,6-tetrahydro-2H-[1,2'; 6',3"]terpyridin-4-yl)ethylcarbamate
23. thiazol-4-ylmethyl 2-(5"-fluoro-3,4,5,6-tetrahydro-2H-[1,2',5',3"]terpyridin-4-yl)ethylcarbamate
24. thiazol-4-ylmethyl 2-(6"-ethoxy-3,4,5,6-tetrahydro-2H-[1,2'; 6',3"]terpyridin-4-yl)ethylcarbamate
25. thiazol-4-ylmethyl (6'-pyrimidin-5-yl-3,4,5,6-tetrahydro-2H-[1,2']bipyridinyl-4-yl)methylcarbamate
26. thiazol-2-ylmethyl{1-[5-(4-fluorophenyl)pyridin-2-yl]pyrrolidin-3-yl)}methylcarbamate
27. thiazol-4-ylmethyl{1-[5-(4-fluorophenyl)pyridin-2-yl]pyrrolidin-3-yl}methylcarbamate
28. thiazol-2-ylmethyl{2-[5'-(4-fluorophenyl)-3,4,5,6-tetrahydro-2H-[1,2']bipyridinyl-4-yl])ethylcarbamate
29. 2,2,2-trifluoro-1-thiazol-2-ylethyl (+/−)-{2-[5'-(4-fluorophenyl)-3,4,5,6-tetrahydro-2H-[1,2]bipyridinyl-4-yl]}ethylcarbamate
30. thiazol-4-ylmethyl{2-[5'-(4-fluorophenyl)-3,4,5,6-tetrahydro-2H-[1,2']bipyridinyl-4-yl]}ethylcarbamate
31. 2,2,2-trifluoro-1-thiazol-4-ylethyl (+/−)-{2-[5'-(4-fluorophenyl)-3,4,5,6-tetrahydro-2H-[1,2']bipyridinyl-4-yl]}ethylcarbamate
32. 2-methylthiazol-4-ylmethyl{2-[5'-(4-fluorophenyl)-3,4,5,6-tetrahydro-2H-[1,2']bipyridinyl-4-yl]}ethylcarbamate
33. thiazol-5-ylmethyl{2-[5'-(4-fluorophenyl)-3,4,5,6-tetrahydro-2H-[1,2']bipyridinyl-4-yl]}ethylcarbamate
34. 2,2,2-trifluoro-1-thiazol-5-ylethyl (+/−)-{2-[5'-(4-fluorophenyl)-3,4,5,6-tetrahydro-2H-[1,2']bipyridinyl-4-yl]}ethylcarbamate
35. thiazol-2-ylmethyl{2-[5'-(4-chlorophenyl)-3,4,5,6-tetrahydro-2H-[1,2']bipyridinyl-4-yl]}ethylcarbamate
36. thiazol-2-ylmethyl{2-[5'-(4-cyanophenyl)-3,4,5,6-tetrahydro-2H-[1,2']bipyridinyl-4-yl]}ethylcarbamate
37. thiazol-5-ylmethyl{2-[5'-(4-cyanophenyl)-3,4,5,6-tetrahydro-2H-[1,2]bipyridinyl-4-yl]}ethylcarbamate
38. thiazol-2-ylmethyl{2-[5'-(4-ethoxyphenyl)-3,4,5,6-tetrahydro-2H-[1,2']bipyridinyl-4-yl]}ethylcarbamate
39. thiazol-4-ylmethyl{2-[5'-(4-ethoxyphenyl)-3,4,5,6-tetrahydro-2H-[1,2']bipyridinyl-4-yl]}ethylcarbamate
40. thiazol-5-ylmethyl{2-[5'-(4-ethoxyphenyl)-3,4,5,6-tetrahydro-2H-[1,2']bipyridinyl-4-yl]}ethylcarbamate
41. thiazol-2-ylmethyl{2-[5'-(3-cyanophenyl)-3,4,5,6-tetrahydro-2H-[1,2']bipyridinyl-4-yl]}ethylcarbamate
42. thiazol-2-ylmethyl{2-[5'-(3-chlorophenyl)-3,4,5,6-tetrahydro-2H-[1,2']bipyridinyl-4-yl]}ethylcarbamate
43. thiazol-4-ylmethyl{2-[5'-(3-carbamoylphenyl)-3,4,5,6-tetrahydro-2H-[1,2']bipyridinyl-4-yl]}ethylcarbamate
44. thiazol-2-ylmethyl{2-[5'-(3-fluorophenyl)-3,4,5,6-tetrahydro-2H-[1,2']bipyridinyl-4-yl]}ethylcarbamate
45. thiazol-4-ylmethyl[6'-(3-trifluoromethylphenyl)-3,4,5,6-tetrahydro-2H-[1,2']bipyridinyl-4-yl]methylcarbamate
46. thiazol-4-ylmethyl{2-[6'-(3-trifluoromethylphenyl)-3,4,5,6-tetrahydro-2H-[1,2']bipyridinyl-4-yl]}ethylcarbamate
47. thiazol-4-ylmethyl[6'-(4-chlorophenyl)-3,4,5,6-tetrahydro-2H-[1,2']bipyridinyl-4-yl]methylcarbamate
48. thiazol-4-ylmethyl{2-[6'-(4-chlorophenyl)-3,4,5,6-tetrahydro-2H-[1,2']bipyridinyl-4-yl]}ethylcarbamate
49. thiazol-2-ylmethyl{2-[6'-4-fluorophenyl)-3,4,5,6-tetrahydro-2H-[1,2']bipyridinyl-4-yl]}ethylcarbamate
50. 2,2,2-trifluoro-1-thiazol-2-ylethyl (+/−)-{2-[6'-(4-fluorophenyl)-3,4,5,6-tetrahydro-2H-[1,2']bipyridinyl-4-yl]}ethylcarbamate 51. thiazol-4-ylmethyl{2-[6'-(4-fluorophenyl)-3,4,5,6-tetrahydro-2H-[1,2']bipyridinyl-4-yl]}ethylcarbamate
52. 2,2,2-trifluoro-1-thiazol-4-ylethyl (+/−)-{2-[6'-(4-fluorophenyl)-3,4,5,6-tetrahydro-2H-[1,2']bipyridinyl-4-yl]}ethylcarbamate
53. 2-methylthiazol-4-ylmethyl{2-[6'-(4-fluorophenyl)-3,4,5,6-tetrahydro-2H-[1,2']bipyridinyl-4-yl]}ethylcarbamate
54. thiazol-5-ylmethyl{2-[6'-(4-fluorophenyl)-3,4,5,6-tetrahydro-2H-[1,2']bipyridinyl-4-yl]}ethylcarbamate
55. 2,2,2-trifluoro-1-thiazol-5-ylethyl (+/−)-{2-[6'-(4-fluorophenyl)-3,4,5,6-tetrahydro-2H-[1,2']bipyridinyl-4-yl]}ethylcarbamate
56. thiazol-4-ylmethyl[6'-(4-methoxyphenyl)-3,4,5,6-tetrahydro-2H-[1,2']bipyridinyl-4-yl]methylcarbamate
57. thiazol-4-ylmethyl{2-[6'-(4-methoxyphenyl)-3,4,5,6-tetrahydro-2H-[1,2']bipyridinyl-4-yl]}ethylcarbamate
58. thiazol-4-ylmethyl[6'-(3-acetylaminophenyl)-3,4,5,6-tetrahydro-2H-[1,2']bipyridinyl-4-yl]methylcarbamate
59. thiazol-4-ylmethyl{2-[6'-(3-acetylaminophenyl)-3,4,5,6-tetrahydro-2H-[1,2']bipyridinyl-4-yl]}ethylcarbamate
60. thiazol-4-ylmethyl[6'43-chlorophenyl)-3,4,5,6-tetrahydro-2H-[1,2']bipyridinyl-4-yl]methylcarbamate
61. thiazol-4-ylmethyl{2-[6'-(3-chlorophenyl)-3,4,5,6-tetrahydro-2H-[1,2']bipyridinyl-4-yl]}ethylcarbamate
62. thiazol-4-ylmethyl (6'-m-tolyl-3,4,5,6-tetrahydro-2H-[1,2']bipyridinyl-4-yl]methylcarbamate
63. thiazol-4-ylmethyl[2-(6'-o-tolyl-3,4,5,6-tetrahydro-2H-[1,2']bipyridinyl-4-yl)]ethylcarbamate
64. thiazol-4-ylmethyl[6'-(2-chlorophenyl)-3,4,5,6-tetrahydro-2H-[1,2']bipyridinyl-4-yl]methylcarbamate
65. thiazol-4-ylmethyl[6'-(3,5-difluorophenyl)-3,4,5,6-tetrahydro-2H-[1,2']bipyridinyl-4-yl]methylcarbamate
66. thiazol-4-ylmethyl{2-[6'-3,5-difluorophenyl)-3,4,5,6-tetrahydro-2H-[1,2']bipyridinyl-4-yl]}ethylcarbamate
67. thiazol-4-ylmethyl[6'-(3,4,5-trimethoxyphenyl)-3,4,5,6-tetrahydro-2H-[1,2']bipyridinyl-4-yl]methylcarbamate
68. thiazol-4-ylmethyl{2-[6'-(2,4-dimethoxyphenyl)-3,4,5,6-tetrahydro-2H-[1,2']bipyridinyl-4-yl]}ethylcarbamate
69. thiazol-4-ylmethyl[6'-(4-isopropylphenyl)-3,4,5,6-tetrahydro-2H-[1,2']bipyridinyl-4-yl]methylcarbamate
70. thiazol-4-ylmethyl{2-[6'-(4-isopropylphenyl)-3,4,5,6-tetrahydro-2H-[1,2']bipyridinyl-4-yl]}ethylcarbamate
71. thiazol-4-ylmethyl[6'-(3-isopropylphenyl)-3,4,5,6-tetrahydro-2H-[1,2']bipyridinyl-4-yl]methylcarbamate
72. thiazol-4-ylmethyl{2-[6'-(3-isopropylphenyl)-3,4,5,6-tetrahydro-2H-[1,2']bipyridinyl-4-yl]}ethylcarbamate
73. thiazol-4-ylmethyl[6'-(4-cyclohexylphenyl)-3,4,5,6-tetrahydro-2H-[1,2']bipyridinyl-4-yl]methylcarbamate
74. thiazol-4-ylmethyl{2-[6'-(4-cyclohexylphenyl)-3,4,5,6-tetrahydro-2H-[1,2']bipyridinyl-4-yl]}ethylcarbamate
75. thiazol-4-ylmethyl[6'-(3-dimethylcarbamoylphenyl)-3,4,5,6-tetrahydro-2H-[1,2']bipyridinyl-4-yl]methylcarbamate
76. thiazol-4-ylmethyl{2-[6'-(3-dimethylcarbamoylphenyl)-3,4,5,6-tetrahydro-2H-[1,2']bipyridinyl-4-yl]}ethylcarbamate
77. thiazol-4-ylmethyl{2-[6'-(4-sulphamoylphenyl)-3,4,5,6-tetrahydro-2H-[1,2']bipyridinyl-4-yl]}ethylcarbamate
78. thiazol-4-ylmethyl[6'-(4-carbamoylphenyl)-3,4,5,6-tetrahydro-2H-[1,2']bipyridinyl-4-yl]methylcarbamate
79. thiazol-4-ylmethyl{2-[6'-(4-carbamoylphenyl)-3,4,5,6-tetrahydro-2H-[1,2']bipyridinyl-4-yl]}ethylcarbamate
80. thiazol-4-ylmethyl[6'-(3-carbamoylphenyl)-3,4,5,6-tetrahydro-2H-[1,2']bipyridinyl-4-yl]methylcarbamate
81. thiazol-4-ylmethyl{2-[6'-(3-carbamoylphenyl)-3,4,5,6-tetrahydro-2H-[1,2']bipyridinyl-4-yl]}ethylcarbamate
82. thiazol-4-ylmethyl[6'-(3-ethylcarbamoylphenyl)-3,4,5,6-tetrahydro-2H-[1,2']bipyridinyl-4-yl]methylcarbamate
83. thiazol-4-ylmethyl{2-[6'-(3-ethylcarbamoylphenyl)-3,4,5,6-tetrahydro-2H-[1,2']bipyridinyl-4-yl]}ethylcarbamate
84. thiazol-4-ylmethyl[6'-(3-propylcarbamoylphenyl)-3,4,5,6-tetrahydro-2H-[1,2']bipyridinyl-4-yl]methylcarbamate
85. thiazol-4-ylmethyl{2-[6'-(4-methanesulphonylaminophenyl)-3,4,5,6-tetrahydro-2H-[1,2]bipyridinyl-4-yl]}ethylcarbamate
86. methyl 4-{4-[(thiazol-4-ylmethoxycarbonylamino)methyl]-3,4,5,6-tetrahydro-2H-[1,2']bipyridinyl-6'-yl}phenylcarbamate
87. methyl 4-{4-[2-(thiazol-4-ylmethoxycarbonylamino)ethyl]-3,4,5,6-tetrahydro-2H-[1,2']bipyridinyl-6'-yl}phenylcarbamate
88. thiazol-4-ylmethyl{2-[6'-(3-pyrrolidin-1-ylphenyl)-3,4,5,6-tetrahydro-2H-[1,2']bipyridinyl-4-yl]}ethylcarbamate
89. thiazol-4-ylmethyl[6'-(2-morpholin-4-ylphenyl)-3,4,5,6-tetrahydro-2H-[1,2']bipyridinyl-4-yl]methylcarbamate
90. thiazol-4-ylmethyl{2-[6'-(2-morpholin-4-ylphenyl)-3,4,5,6-tetrahydro-2H-[1,2']bipyridinyl-4-yl]}ethylcarbamate
91. thiazol-4-ylmethyl{2-[6'-(3-ethoxyphenyl)-3,4,5,6-tetrahydro-2H-[1,2']bipyridinyl-4-yl]}ethylcarbamate
92. thiazol-4-ylmethyl{2-[6'-(4-cyclopropylmethoxyphenyl)-3,4,5,6-tetrahydro-2H-[1,2']bipyridinyl-4-yl]}ethylcarbamate
93. thiazol-4-ylmethyl[6'-(3-cyclopropylmethoxyphenyl)-3,4,5,6-tetrahydro-2H-[1,2']bipyridinyl-4-yl]methylcarbamate
94. thiazol-4-ylmethyl{2-[6"-(3-cyclopropylmethoxyphenyl)-3,4,5,6-tetrahydro-2H-[1,2']bipyridinyl-4-yl]}ethylcarbamate
95. thiazol-4-ylmethyl[6'-(4-cyanomethylphenyl)-3,4,5,6-tetrahydro-2H-[1,2']bipyridinyl-4-yl]methylcarbamate
96. thiazol-4-ylmethyl[6'-(3-cyanomethylphenyl)-3,4,5,6-tetrahydro-2H-[1,2']bipyridinyl-4-yl]methylcarbamate
97. thiazol-4-ylmethyl{6'-[4-(piperidine-1-sulphonyl)phenyl]-3,4,5,6-tetrahydro-2H-[1,2']bipyridinyl-4-yl]}methylcarbamate
98. thiazol-4-ylmethyl (2-{6'-[4-(piperidine-1-sulphonyl)phenyl]-3,4,5,6-tetrahydro-2H-[1,2']bipyridinyl-4-yl})ethylcarbamate
99. thiazol-4-ylmethyl[6-(4-acetylaminophenyl)-3,4,5,6-tetrahydro-2H-[1,2']bipyridinyl-4-yl]methylcarbamate
100. thiazol-4-ylmethyl{2-[6'-(4-acetylaminophenyl)-3,4,5,6-tetrahydro-2H-[1,2']bipyridinyl-4-yl]}ethylcarbamate
101. thiazol-4-ylmethyl{2-[6'-(3-methanesulphonylphenyl)-3,4,5,6-tetrahydro-2H-[1,2']bipyridinyl-4-yl]}ethylcarbamate
102. thiazol-4-ylmethyl[6'-(3-ethanesulphonylphenyl)-3,4,5,6-tetrahydro-2H-[1,2']bipyridinyl-4-yl]methylcarbamate
103. thiazol-4-ylmethyl{2-[6'-(3-ethanesulphonylphenyl)-3,4,5,6-tetrahydro-2H-[1,2']bipyridinyl-4-yl]}ethylcarbamate
104. thiazol-2-ylmethyl{2-[1-(6-chloroquinolin-2-yl)piperidin-4-yl]}ethylcarbamate
105. 4-trifluoromethylthiazol-2-ylmethyl{2-[1-(6-chloroquinolin-2-yl)piperidin-4-yl]}ethylcarbamate
106. 2,2,2-trifluoro-1-thiazol-2-ylethyl (+/−)-{2-[1-(6-chloroquinolin-2-yl)piperidin-4-yl]}ethylcarbamate
107. 1-thiazol-4-ylethyl (+/−)-{2-[1-(6-chloroquinolin-2-yl)piperidin-4-yl]}ethylcarbamate
108. 2,2,2-trifluoro-1-thiazol-4-ylethyl (+/−)-{2-[1-(6-chloroquinolin-2-yl)piperidin-4-yl]}ethylcarbamate
109. thiazol-4-ylmethyl{2-[1-(6-chloroquinolin-2-yl)piperidin-4-yl]}ethylcarbamate 110. 2-methylthiazol-4-ylmethyl{2-[1-(6-chloroquinolin-2-yl)piperidin-4-yl]}ethylcarbamate
111. 2-trifluoromethylthiazol-4-ylmethyl{2-[1-(6-chloroquinolin-2-yl)piperidin-4-yl]}-ethylcarbamate
112. 2-chlorothiazol-4-ylmethyl{2-[1-(1-chloroquinolin-2-yl)piperidin-4-yl]}ethylcarbamate
113. 2-pyridin-3-ylthiazol-4-ylmethyl{2-[1-(6-chloroquinolin-2-yl)piperidin-4-yl]}ethylcarbamate
114. 2-pyridin-4-ylthiazol-5-ylmethyl{2-[1-(6-chloroquinolin-2-yl)piperidin-4-yl]}ethylcarbamate
115. thiazol-5-ylmethyl{2-[1-(6-chloroquinolin-2-yl)piperidin-4-yl]}ethylcarbamate
116. 2,2,2-trifluoro-1-thiazol-5-ylethyl (+/−)-{2-[1-(6-chloroquinolin-2-yl)piperidin-4-yl]}ethylcarbamate
117. thiazol-5-ylmethyl{2-[1-(6-fluoroquinolin-2-yl)piperidin-4-yl]}ethylcarbamate
118. thiazol-5-ylmethyl{2-[1-(7-fluoroquinolin-2-yl)piperidin-4-yl]}ethylcarbamate
119. thiazol-4-ylmethyl (6'-naphthalen-1-yl-3,4,5,6-tetrahydro-2H-[1,2']bipyridinyl-4-yl)methylcarbamate
120. thiazol-4-ylmethyl[2-(6'-naphthalen-1-yl-3,4,5,6-tetrahydro-2H-[1,2']bipyridinyl-4-yl)]ethylcarbamate
121. thiazol-4-ylmethyl (6'-naphthalen-2-yl-3,4,5,6-tetrahydro-2H-[1,2]bipyridinyl-4-yl)methylcarbamate
122. thiazol-4-ylmethyl (6'-naphthalen-2-yl-3,4,5,6-tetrahydro-2H-[1,2']bipyridinyl-4-yl)ethylcarbamate
123. thiazol-4-ylmethyl (6'-quinolin-4-yl-3,4,5,6-tetrahydro-2H-[1,2']bipyridinyl-4-yl)methylcarbamate
124. thiazol-4-ylmethyl[2-(6'-quinolin-4-yl-3,4,5,6-tetrahydro-2H-[1,2]bipyridinyl-4-yl)]ethylcarbamate
125. thiazol-4-ylmethyl (6'-quinolin-6-yl-3,4,5,6-tetrahydro-2H-[1,2]bipyridinyl-4-yl)methylcarbamate
126. thiazol-4-ylmethyl[2-(6'-quinolin-6-yl-3,4,5,6-tetrahydro-2H-[1,2]bipyridinyl-4-yl)]ethylcarbamate
127. thiazol-4-ylmethyl (6'-isoquinolin-4-yl-3,4,5,6-tetrahydro-2H-[1,2']bipyridinyl-4-yl)methylcarbamate
128. thiazol-4-ylmethyl[2-(6'-isoquinolin-4-yl-3,4,5,6-tetrahydro-2H-[1,2']bipyridinyl-4-yl)]ethylcarbamate
129. thiazol-4-ylmethyl (6'-isoquinolin-5-yl-3,4,5,6-tetrahydro-2H-[1,2']bipyridinyl-4-yl)methylcarbamate
130. thiazol-4-ylmethyl (6'-isoquinolin-5-yl-3,4,5,6-tetrahydro-2H-[1,2']bipyridinyl-4-yl)ethylcarbamate
131. 2-carbamoythiazol-4-ylmethyl 2-[5-(4-fluorophenyl]-3,4,5,6-tetrahydro-2H-[1,2']bipyridinyl-4-yl]ethylcarbamate
132. 2-methylcarbamoylthiazol-4-ylmethyl 2-[5'-(4-fluorophenyl)-3,4,5,6-tetrahydro-2H-[1,2']bipyridinyl-4-yl]ethylcarbamate
133. 4-carbamoylthiazol-2-ylmethyl 2-[5'-(4-fluorophenyl)-3,4,5,6-tetrahydro-2H-[1,2']bipyridinyl-4-yl]ethylcarbamate
134. 4-methylcarbamoylthiazol-2-ylmethyl 2-[5'-(4-fluorophenyl)-3,4,5,6-tetrahydro-2H-[1,2']bipyridinyl-4-yl]ethylcarbamate in the form of the base or an addition salt with an acid.

The compounds of general formula (I) may include one or more asymmetric carbons. They may exist in the form of enantiomers or diastereoisomers. The compounds of general formula (I) may also exist in the form of cis [Z] or trans [E] stereoisomers. These stereoisomers, enantiomers and diastereoisomers, and also mixtures thereof, including the racemic mixtures, form part of the invention.

The compounds of formula (I) may exist in the form of bases or of addition salts with acids. Addition salts of this kind form part of the invention.

These salts are advantageously prepared with pharmaceutically acceptable acids, although the salts of other acids useful, for example, for purifying or isolating the compounds of formula (I) likewise form part of the invention, In the context of the invention, the terms are understood as follows:

$C_{t-z}$, where t and may take the values from 1 to 8, is a carbon chain which may have from t to z carbon atoms; for example, $C_{1-3}$ is a carbon chain which may have from 1 to 3 carbon atoms;

alkyl is a saturated, linear or branched aliphatic group; for example, a $C_{1-6}$ alkyl group represents a linear or branched carbon chain of 1 to 6 carbon atoms, more particularly a methyl, ethyl, propyl, isopropyl, butyl, isobutyl, tert-butyl, pentyl or hexyl;

alkylene is a saturated, linear or branched divalent alkyl group; for example, a $C_{1-3}$ alkylene group represents a linear or branched, divalent carbon chain of 1 to 3 carbon atoms, more particularly a methylene, ethylene, 1-methylethylene or propylene;

cycloalkyl is a cyclic alkyl group; for example, a $C_{3-7}$ cycloalkyl group represents a cyclic carbon group of 3 to 7 carbon atoms, more particularly a cyclopropyl, cyclobutyl, cyclopentyl, cyclohexyl or cycloheptyl;

alkoxy is an —O-alkyl group having a saturated, linear or branched aliphatic chain;

thioalkyl is an —S-alkyl group having a saturated, linear or branched aliphatic chain;

haloalkyl is an alkyl group in which one or more hydrogen atoms have been substituted by a halogen atom;

haloalkoxy is an alkoxy group in which one or more hydrogen atoms have been substituted by a halogen atom;

halothioalkyl is a thioalkyl group in which one or more hydrogen atoms have been substituted by a halogen atom;

a halogen atom is a fluorine, chlorine, bromine or iodine;

"(+/−)" denotes a compound in the form of the racemic mixture.

The compounds of the invention may be prepared by various methods, these methods being illustrated by the schemes below.

Thus a first method (scheme 1) comprises reacting an amine of general formula (II) in which A, $R_1$, $R_2$, m and n are as defined in the general formula (I) defined above with a carbonate of general formula (III) in which Z represents a hydrogen atom or a nitro group and $R_3$ and $R_4$ are as defined in the general formula (I) defined above, in the presence of a base such as triethylamine, pyridine, N,N-dimethylaminopyridine or diisopropylethylamine, in a solvent such as toluene or dichloroethane, at a temperature between the ambient temperature and the reflux temperature of the solvent.

One variant way of obtaining compounds of general formula (I) (scheme 1) comprises reacting an amine of general formula (II) as defined above with phenyl or 4-nitrophenyl chloroformate in the presence of a base such as triethylamine or diisopropylethylamine, in a solvent such as dichloromethane or tetrahydrofuran, at a temperature between 0° C. and the ambient temperature, to give the carbamate derivative of general formula (IV) in which A, $R_1$, $R_2$, m and n are as defined in the general formula (I) defined above, and Z represents a hydrogen atom or a nitro group. The carbamate derivative of general formula (IV) thus obtained is then converted into a compound of general formula (I) by the action of an alcohol of general formula $HOCHR_3R_4$ (IIIa), in which $R_3$ and $R_4$ are as defined in the general formula (I) defined above, in the presence of a base such as triethylamine, pyridine, N,N-dimethylaminopyridine or diisopropylethylamine, in a solvent such as toluene or dichloroethane, at a temperature between the ambient temperature and the reflux temperature of the solvent.

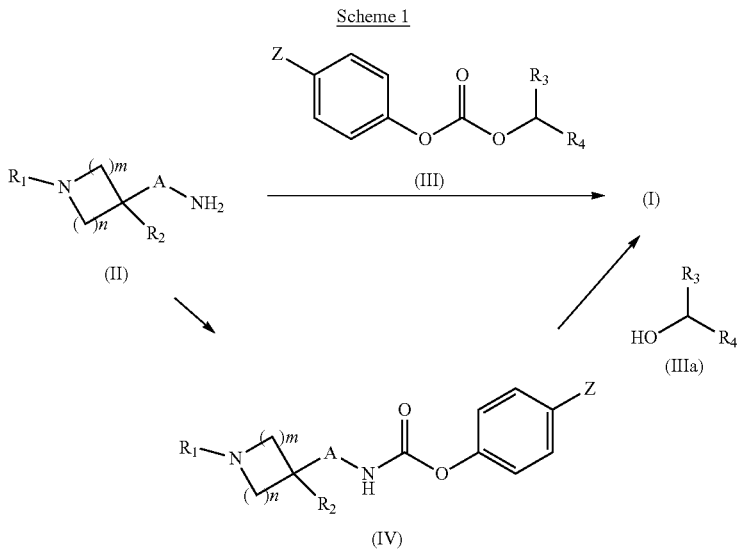

A second method (scheme 2) comprises reacting, in a first stage, an amine of general formula (IIa) in which A, $R_2$, m and n are as defined in the general formula (I) defined above, and PG represents a protecting group such as a Boc (tert-butyloxycarbonyl), a Cbz (benzyloxycarbonyl), a benzyl or a benzhydryl, with a carbonate of general formula (III) as defined above, under the conditions described above for the reaction of the amine of general formula (II) with the carbonate of general formula (III), followed by a deprotecting reaction, for example in the presence of a solution of hydrochloric acid (5N) in isopropanol or dioxane, to give the intermediate of general formula (Ia) in which A, $R_2$, $R_3$, $R_4$, m and n are as defined in the general formula (I).

One variant way of obtaining intermediates of general formula (Ia) (scheme 2) comprises reacting an amine of general formula (IIa) as defined above with phenyl or 4-nitrophenyl chloroformate in the presence of a base such as triethylamine or diisopropylethylamine, in a solvent such as dichloromethane or tetrahydrofuran, at a temperature between 0° C. and the ambient temperature, to give the carbamate derivative of general formula (IVa) in which A. $R_2$, m and n are as defined in the general formula (I) defined above. PG is as defined above and Z represents a hydrogen atom or a nitro group. The carbamate derivative of general formula (IVa) thus obtained is subsequently converted into a compound of general formula (Ia) by the action of an alcohol of general formula HOCHR$_3$R$_4$ (IIIa) as defined above, in the presence of a base such as triethylamine, pyridine, N,N-dimethylaminopyridine or diisopropylethylamine, in a solvent such as toluene or dichloroethane, at a temperature between the ambient temperature and the reflux temperature of the solvent, followed by a deprotecting reaction, for example in the presence of a solution of hydrochloric acid (5N) in isopropanol or dioxane.

The compound of general formula (I) is then obtained by reacting the compound of general formula (Ia) with a derivative of general formula (V) in which $R_1$ is as defined in the general formula (I) and $U_1$ represents a halogen atom or an O-triflate group, utilizing the conditions of aromatic or heteroaromatic nucleophilic substitution reactions, by means for example of a base such as triethylamine, diisopropylamine, pyridine or N,N-dimethylaminopyridine in a solvent such as dichloromethane, dichloroethane, acetonitrile. N,N-dimethylformamide, dioxane or tetrahydrofuran, at a temperature between 0° C. and the reflux temperature of the solvent. This conversion may also be performed using the Buchwald N-arylation or N-heteroarylation conditions, for example by means of a palladium or copper catalyst.

According to scheme 2 the compounds of general formula (I) in which $R_1$ represents a group $R_5$ which is substituted in particular by a group $R_6$ of $C_{1-6}$ alkyl, $C_{3-7}$ cycloalkyl or $C_{3-7}$ cycloalkyl-$C_{1-3}$ alkylene type, or by a group $R_7$ as defined in the general formula (I) defined above, may also be prepared by a coupling reaction, catalysed by means of a transition metal, for example palladium(0), performed on the compound of general formula (Ib) in which A, $R_2$, $R_3$, $R_4$, $R_5$, m and n are as defined in the general formula (I) and $U_2$ represents a chlorine, bromine or iodine atom or a triflate group. $U_2$ being in the position in which it is desired to introduce the group $R_6$ or $R_7$ (scheme 2):
alternatively by a Suzuki reaction, for example by means of an alkyl-, cycloalkyl-, aryl- or heteroaryl-boronic acid,
or by a Stille reaction, for example using an aryl or heteroaryl trialkyltin derivative
or by a Negishi reaction, for example using an alkyl, cycloalkyl, aryl or heteroaryl halide zincate derivative.

The intermediate of general formula (Ib) as defined above is obtained beforehand by reacting an amine of general formula (Ia) as defined above with a derivative of general formula (Va) in which $R_5$, $U_1$ and $U_2$ are as defined above, utilizing aromatic or heteroaromatic nucleophilic substitution reactions or Buchwald N-arylation or N-heteroarylation reactions, for example by means of a palladium or copper catalyst.

One variant way of obtaining intermediates of general formula (Ib) (scheme 2) comprises reacting, in a first stage, an amine of general formula (IIb) in which A, $R_5$, $R_2$, m and n are as defined in the general formula (I) defined above, and $U_2$ is as defined above, with a carbonate of general formula (III) as defined above, under the conditions described above for the reaction of the amine of general formula (II) with the carbonate of general formula (III), to give the intermediate of general formula (Ib) in which A. $R_5$, $R_2$, $R_3$, $R_4$, m and n are as defined in the general formula (I), and $U_2$ is as defined above.

Scheme 2

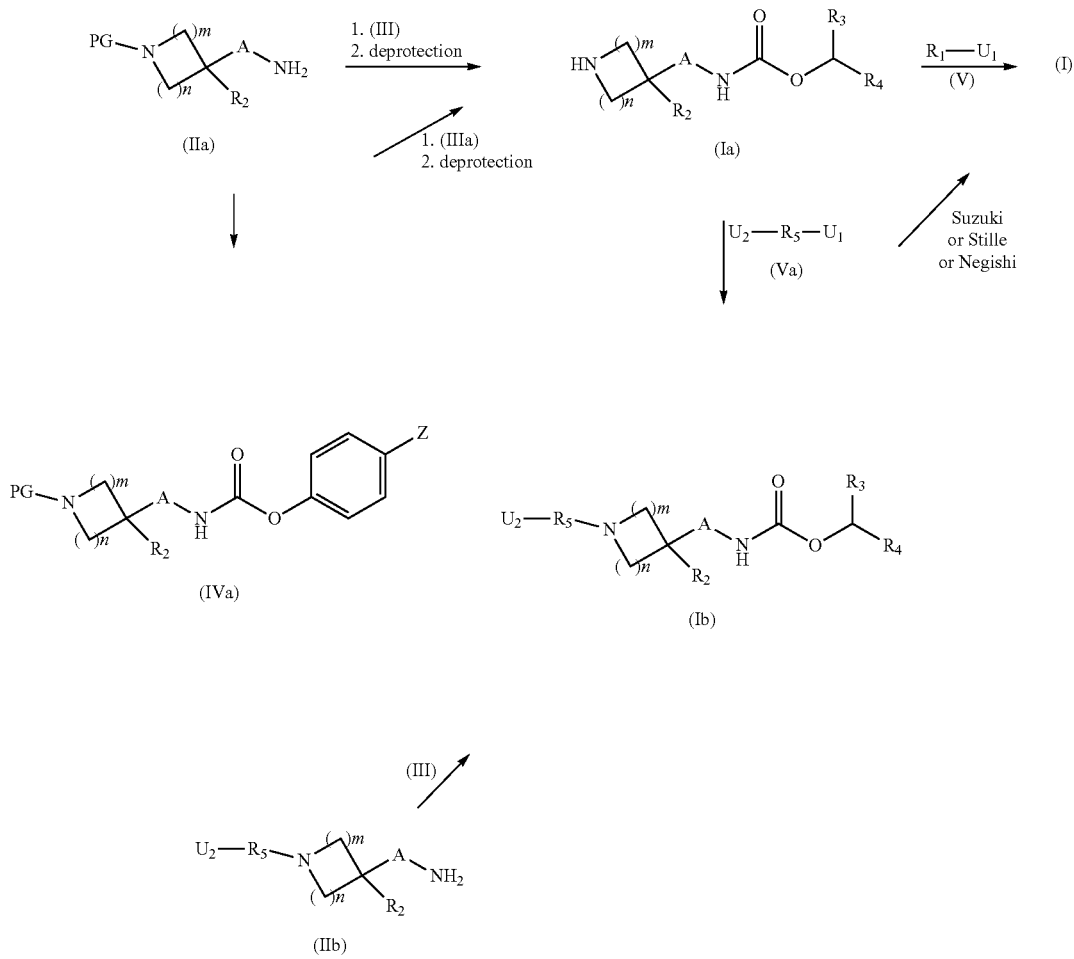

The compounds of general formulae (II), (IIa), (IIb), (III), (IIIa), (V) and (Va) and also the other reactants are available commercially or are described in the literature, or else may be prepared by methods which are described therein or which are known to a person skilled in the art.

In particular the carbonate of general formula (III) may be prepared by any method described in the literature, for example by reaction of an alcohol of general formula HOCHR$_3$R$_4$ (IIIa), in which R$_3$ and R$_4$ are as defined in the general formula (I) as defined above, with phenyl or 4-nitrophenyl chloroformate, in the presence of a base such as triethylamine. N-methyl-morpholine or diisopropylethylamine, in a solvent such as dichloromethane or tetrahydrofuran, at a temperature between 0° C. and the ambient temperature.

The examples which follow illustrate the preparation of a number of compounds of the invention. These examples are not limiting and serve merely to illustrate the invention. The microanalyses, the IR and NMR spectra and/or the LC-MS (liquid chromatography coupled to mass spectroscopy) confirm the structures and the purities of the compounds obtained.

m.p. (° C.) represents the melting point in degrees Celsius,

The numbers between brackets in the titles of the examples correspond to those in the 1$^{st}$ column of the subsequent table.

IUPAC (International Union of Pure and Applied Chemistry) nomenclature has been used for the naming of the compounds in the examples below.

EXAMPLE 1

Compound 30

Thiazol-4-ylmethyl 2-[5'-(4-fluorophenyl)-3,4,5,6-tetrahydro-2H-[1,2']bipyridinyl-4-yl]ethylcarbamate

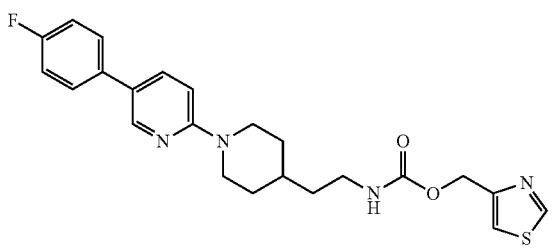 [SMILES: O=C(NCCC1CCN(c2ccc(-c3ccc(F)cc3)cn2)CC1)OCc1cscn1]

1.1. 2-(5'-Bromo-3,4,5,6-tetrahydro-2H-[1,2']bipyridinyl-4-yl)ethanol

An autoclave is charged with 11 g (46.43 mmol) of 2,5-dibromopyridine, 6 g (46.43 mmol) of piperidin-4-ylethanol and 6.74 g (48.76 mmol) of potassium carbonate in 8 ml of DMSO. This charge is subsequently heated at 160° C. for 20 hours.

Following return to ambient temperature, the reaction mixture is taken up in ethyl acetate and water. The aqueous phase is separated off and extracted twice with ethyl acetate, the combined organic phases are washed with saturated aqueous sodium chloride solution and dried over sodium sulphate, and the filtrate is concentrated under reduced pressure.
This gives 11 g of product in the form of an oil, which is used as it is in the following step.

1.2. 2-[5'-(4-Fluorophenyl)-3,4,5,6-tetrahydro-2H-[1,2']bipyridinyl-4-yl]ethanol Under an inert atmosphere, 3.6 g (12.62 mmol) of 2-(5'-bromo-3,4,5,6-tetrahydro-2H-[1,2']bipyridinyl-4-yl)ethanol, prepared in step 1.1., 3.53 g (25.25 mmol) of 4-fluorophenylboronic acid, 5.23 g (37.87 mmol) of potassium carbonate and 4.88 g (15.15 mmol) of tetrabutylammonium bromide in suspension in 20 ml of water are introduced. Subsequently, 0.142 g (0.63 mmol) of Pd(OAc)$_2$ is added. The reaction mixture is subsequently heated at reflux for 24 hours.

Following return to ambient temperature, the salts are separated by filtration on Celite, and than the filtrate is taken up in ethyl acetate; the aqueous phase is separated off and extracted twice with ethyl acetate, and the combined organic phases are washed with saturated aqueous sodium chloride solution and dried over sodium sulphate. Following evaporation of the solvent, the residue obtained is purified by chromatography on silica gel, eluting with a 50/50 mixture of ethyl acetate and cyclohexane.

This gives 1.6 g of product in the form of a white powder.
m.p. (° C.)=118-120° C.

1.3. 2-{2-[5'-(4-Fluorophenyl)-3,4,5,6-tetrahydro-2H-[1,2']bipyridinyl-4-yl]ethyl}isoindole-1,3-dione A solution of 2 g (6.66 mmol) of 2-[5'-(4-fluorophenyl)-3,4,5,6-tetrahydro-2H-[1,2']bipyridinyl-4-yl]ethanol, prepared in step 1.2., 2.096 g (7.99 mmol) of triphenylphosphine and 1.077 g (7.32 mmol) of phthalimide in 40 ml of tetrahydrofuran, cooled to approximately −2° C., is admixed dropwise under an inert atmosphere with a solution of 1.61 g (7.99 mmol) of diisopropyl azodicarboxylate (DIAD) in 4 ml of tetrahydrofuran, the temperature of the reaction mixture being maintained at between −2° C. and 0° C. Stirring is continued at 0° C. for 1 hour, and then at ambient temperature for 12 hours. The reaction mixture is concentrated under reduced pressure the residue is taken up in dichloromethane and water. The aqueous phase is separated off and then extracted twice with dichloromethane. The organic phases are combined and washed in succession with aqueous hydrochloric acid (1N), then with saturated aqueous sodium hydrogencarbonate solution and saturated aqueous sodium chloride solution. The organic phase is dried over sodium sulphate and the filtrate is concentrated under reduced pressure. The resulting residue is purified by chromatography on silica gel, eluting with a 20/80 mixture of ethyl acetate and cyclohexane.

This gives 2.1 g of the expected product in the form of a white powder.
m.p. (° C.)=180-182° C.

1.4. 2-[5'-(4-Fluorophenyl)-3,4,5,6-tetrahydro-2H-[1,2']bipyridinyl-4-yl]ethylamine A solution of 1.3 g (3.03 mmol) of 2-{2-[5'-(4-fluorophenyl)-3,4,5,6-tetrahydro-2H-[1,2']bipyridinyl-4-yl]ethyl}isoindole-1,3-dione, prepared in step 1.3., in 30 ml of ethanol is admixed slowly at ambient temperature with 0.485 g (15.13 mmol) of hydrazine monohydrate. The reaction mixture is subsequently heated at reflux for three hours.

Following return to ambient temperature, the insoluble material is separated off by filtration and the filtrate is concentrated under reduced pressure. The residue is taken up in 20 ml of ether and is left with stirring at ambient temperature for an hour. The insoluble material is separated off again and the filtrate is concentrated under reduced pressure.

This gives 0.70 g of the expected product in the form of a white powder.
m.p. (° C.)=88-94° C.
$^1$H NMR (CDCl$_3$) δ (ppm): 8.3 (d, 1H); 7.55 (dd, 1H); 7.35 (m, 2H); 7.05 (d, 1H); 7.1 (d, 1H); 6.65 (d, 1H); 4.25 (broad d, 2H); 3.0-2.8 (m, 4H); 1.8 (m, 2H); 1.6-1.1 (m, 5H).

1.5. Thiazol-4-ylmethyl 2-[5'-(4-fluorophenyl)-3,4,5,6-tetrahydro-2H-[1,2']bipyridinyl-4-yl]ethylcarbamate A solution of 0.3 g (1.07 mmol) of 2-[5'-(4-fluorophenyl)-3,4,5,6-tetrahydro-2H-[1,2']bipyridinyl-4-yl]ethylamine, prepared in step 1.4., 0.35 g (1.18 mmol) of thiazol-4-ylmethyl (4-nitrophenyl)carbonate (WO2008/013834) and 0.21 g (1.61 mmol) of N,N-diisopropylethylamine in 5 ml of 1,2-dichloroethane is heated at 70° C. for 12 hours.

Following return to ambient temperature, the insoluble material is separated off by filtration and the filtrate is concentrated under reduced pressure. The residue is taken up in dichloromethane and water, the aqueous phase is separated off and extracted three times with dichloromethane, and the combined organic phases are washed with saturated aqueous sodium chloride solution and dried over sodium sulphate. Following evaporation of the solvent, the residue obtained is purified by chromatography on silica gel, eluting with a 95/5 mixture of dichloromethane and methanol.

This gives 0.3 g of pure product in the form of a white powder.
LC-MS: M+H=441
m.p. (° C.): 130-132° C.
$^1$H NMR (DMSO) δ (ppm): 9.1 (s, 1H); 8.45 (s, 1H); 7.85 (d, 1H); 7.7 (m, 4H); 7.3 (m, 2H); 6.95 (d, 1H); 5.15 (s, 2H);

4.30 (broad d, 2H); 3.1 (m, 2H); 2.8 (m, 2H); 1.8 (m, 2H); 1.6 (m, 1H); 1.4 (m, 2H); 1.1 (m, 2H).

EXAMPLE 2

Compound 28

Thiazol-2-ylmethyl 2-[5'-(4-fluorophenyl)-3,4,5,6-tetrahydro-2H-[1,2']bipyridinyl-4-yl]-ethylcarbamate

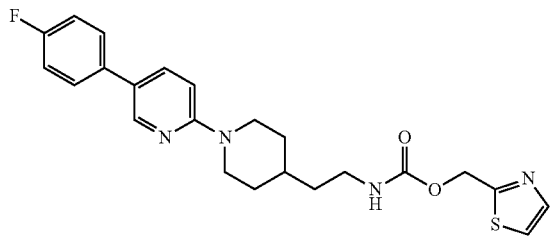 [SMILES: O=C(NCCC1CCN(c2ccc(-c3ccc(F)cc3)cn2)CC1)OCc1nccs1]

The procedure described in Example 1 (step 1.4.) is followed. Starting from 0.3 g (1.07 mmol) of 2-[5'-(4-fluorophenyl)-3,4,5,6-tetrahydro-2H-[1,2]bipyridinyl-4-yl]ethylamine, described in Example 1 (step 1.3.) and 0.35 g (1.18 mmol) of thiazol-2-ylmethyl (4-nitrophenyl)carbonate (EP486948A2), and after chromatography on silica gel, eluting with a 98/2 mixture of dichloromethane and methanol, gives 0.25 g of pure product in the form of a white powder.

LC-MS: M+H=441
m.p. (° C.): 131-133° C.
$^1$H NMR (DMSO) δ (ppm): 8.45 (s, 1H); 7.80 (m, 3H); 7.65 (dd, 2H); 7.45 (m, 1H); 7.25 (dd, 2H); 6.9 (d, 1H); 5.30 (s, 2H); 4.30 (broad d, 2H); 31 (m, 2H); 2.8 (m, 2H); 1.75 (m, 2H); 1.6 (m, 1H); 1.4 (m, 2H); 1.1 (m, 2H).

EXAMPLE 3

Compound 33

Thiazol-5-ylmethyl 2-[5'-(4-fluorophenyl)-3,4,5,6-tetrahydro-2H-[1,2']bipyridinyl-4-yl]ethylcarbamate

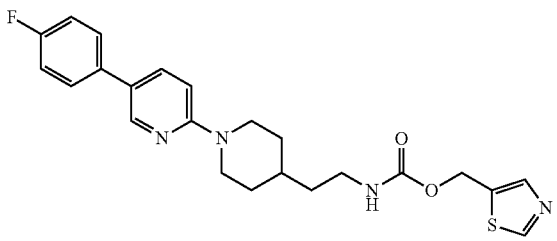 [SMILES: O=C(NCCC1CCN(c2ccc(-c3ccc(F)cc3)cn2)CC1)OCc1cncs1]

The procedure described in Example 1 (step 1.4.) is followed. Starting from 0.16 g (0.53 mmol) of 2-[5'-(4-fluorophenyl)-3,4,5,6-tetrahydro-2H-[1,2']bipyridinyl-4-yl]ethylamine, described in Example 1 (step 1.3.) and 0.22 g (0.8 mmol) of thiazol-5-ylmethyl (4-nitrophenyl)carbonate, and after chromatography on silica gel, eluting with a 40/60 mixture of ethyl acetate and cyclohexane, gives 0.180 g of pure product in the form of a white powder.

LC-MS: M+H=441
m.p. (° C.): 100-102° C.
$^1$H NMR (DMSO) δ (ppm): 9.1 (s, 1H); 8.4 (broad s, 1H); 7.9 (s, 1H); 7.8 (dd, 1H); 7.60 (dd, 2H); 7.20 (m, 3H); 6.90 (d, 1H); 5.2 (s, 2H); 4.30 (broad d, 2H); 3 (m, 2H); 2.75 (m, 2H); 1.8-1.1 (m, 7H).

EXAMPLE 4

Compound 50

2,2,2-Trifluoro-1-thiazol-2-ylethyl (+/−)-2-[6'-(4-fluorophenyl)-3,4,5,6-tetrahydro-2H-[1,2']bipyridinyl-4-yl]ethylcarbamate

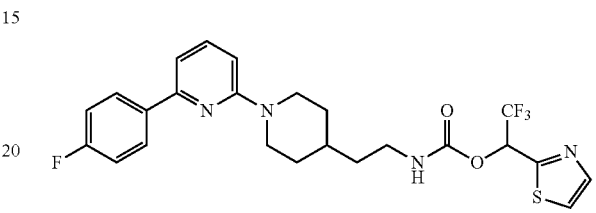

4.1 2-[6'-(4-Fluorophenyl)-3,4,5,6-tetrahydro-2H-[1,2]bipyridinyl-4-yl]ethanol

Under an inert atmosphere, 3.6 g (12.62 mmol) of 2-(6'-bromo-3,4,5,6-tetrahydro-2H-[1,2']bipyridinyl-4-yl)ethanol (WO2004/099176), 3.53 g (25.25 mmol) of 4-fluorophenylboronic acid, 5.23 g (37.87 mmol) of potassium carbonate and 4.88 g (15.15 mmol) of tetrabutylammonium bromide in suspension in 20 ml of water are introduced. Subsequently 0.142 g (0.63 mmol) of Pd(OAc)$_2$ is added. The reaction mixture is subsequently heated at reflux for 24 hours.

Following return to ambient temperature, the salts are separated off by filtration on Celite, and then the filtrate is taken up in ethyl acetate; the aqueous phase is separated off and extracted twice with ethyl acetate, and the combined organic phases are washed with saturated aqueous sodium chloride solution and dried over sodium sulphate. Following evaporation of the solvent, the residue obtained is purified by chromatography on silica gel, eluting with a 99/1 mixture of dichloromethane and methanol.

This gives 3.6 g of product in the form of a white powder.
m.p. (° C.)=96-100° C.

4.2. 2-{2-[6'-(4-Fluorophenyl)-3,4,5,6-tetrahydro-2H-[1,2']bipyridinyl-4-yl]ethyl}isoindole-1,3-dione The procedure described in Example 1 (step 1.2.) is followed, Starting from g (6.66 mmol) of 2-[6'-(4-fluorophenyl)-3,4,5,6-tetrahydro-2H-[1,2']bipyridinyl-4-yl]ethanol, prepared in step 4.1., 2.096 g (7.99 mmol) of triphenylphosphine, 1.077 g (7.32 mmol) of phthalimide and 1.61 g (7.99 mmol) of diisopropyl azodicarboxylate (DIAD), and after chromatography on silica gel, eluting with a 15/85 mixture of ethyl acetate and cyclohexane, gives 1.4 g of pure product in the form of a white powder.
m.p. (° C.)=112-114° C.

4.3. 2-[6'-(4-Fluorophenyl)-3,4,5,6-tetrahydro-2H-[1,2']bipyridinyl-4-yl]ethylamine The procedure described in Example 1 (step 1.3.) is followed. Starting from 1.3 g (3.03 mmol) of 2-{2-[6'-(4-fluorophenyl)-3,4,5,6-tetrahydro-2H-[1,2']bipyridinyl-4-yl]

ethyl}isoindole-1,3-dione, prepared in step 4.2., and 0.485 g (15.13 mmol) of hydrazine monohydrate gives 0.8 g of product in the form of a colourless liquid, which is used as it is in the following step.

$^1$H NMR (CDCl$_3$) δ (ppm): 8.2 (d, 1H); 8.15 (d, 1H); 775 (dd, 1H); 7.35 (broad t, 2H); 7.2 (d, 1H); 6.75 (d, 1H); 4.75 (broad d, 2H); 3.2-3.0 (m, 4H); 2.15 (m, 2H); 1.8-1.3 (m, 5H).

4.4. 4-Nitrophenyl 2-[6'-(4-fluorophenyl-3,4,5,6-tetrahydro-2H-[1,2']bipyridinyl-4-yl]ethylcarbamate A solution of 5 g (16.7 mmol) of 2-[6'-(4-fluorophenyl)-3,4,5,6-tetrahydro-2H-[1,2']bipyridinyl-4-yl]ethylamine, prepared in step 4.3., 4.32 g (33.40 mmol) of N,N-diisopropylethylamine and 0.10 g (0.84 mmol) of N,N-dimethylaminopyridine in 80 ml of dichloromethane, cooled to approximately 0° C., is admixed in small portions with 3.7 g (18.37 mmol) of 4-nitrophenyl chloroformate. Stirring is continued at 0° C. for 1 hour and then at ambient temperature for 2 hours.

Water is added to the reaction mixture, the aqueous phase is separated off and extracted a number of times with dichloromethane, the combined organic phases are washed with saturated aqueous sodium chloride solution and dried over sodium sulphate, and the filtrate is concentrated under reduced pressure.

Chromatography on silica gel, eluting with a 98/2 mixture of dichloromethane and methanol, gives 4.6 g of pure product in the form of a white powder.

m.p. (° C.): 138-142° C.

4.5. 2,2,2-Trifluoro-1-thiazol-2-ylethanol

A solution of 2 g (17.68 mmol) of thiazole-2-carboxaldehyde and 0.88 ml (0.88 mmol) of a 1M solution of tetrabutylammonium fluoride in THF, in 88 ml of THF, is admixed slowly at approximately 0° (ice bath) with 2.7 g (19.44 mmol) of trifluoromethyltrimethylsilane (TMS-CF$_3$). Stirring is continued at ambient temperature for 2 hours. The reaction mixture is admixed with 25 ml of 1N aqueous hydrochloric acid and ethyl acetate. The aqueous phase is separated off and extracted twice with ethyl acetate, and the combined organic phases are washed successively with saturated aqueous sodium bicarbonate solution and than with saturated aqueous sodium chloride solution and are dried over sodium sulphate. Following evaporation of the solvent, the residue obtained is purified by chromatography on silica gel, eluting with a 98/2 mixture of dichloromethane and methanol.

This gives 2.33 g of product in the form of a beige solid.
m.p. (° C.): 90-92° C.

4.6. 2,2,2-Trifluoro-1-thiazol-2-ylethyl (+/−)-2-[6'-(4-fluorophenyl)-3,4,5,6-tetrahydro-2H-[1,2']bipyridinyl-4-yl]ethylcarbamate A solution of 0.465 g (1 mmol) of 4-nitrophenyl 2-[6'-(4-fluorophenyl)-3,4,5,6-tetrahydro-2H-[1,2']bipyridinyl-4-yl]ethylcarbamate, prepared in step 4.4., 0.19 g (1.5 mmol) of N,N-diisopropylethylamine, 0.006 g (0.05 mmol) of N,N-dimethylaminopyridine and 0.20 g (1.1 mmol) of 2,2,2-trifluoro-1-thiazol-2-ylethanol, obtained in step 4.5., in 5 ml of 1,2-dichloroethane is heated at 80° C. for 12 hours.

Following return to ambient temperature, the insoluble material is separated off by filtration and the filtrate is concentrated under reduced pressure. The residue is taken up in dichloromethane and water, the aqueous phase is separated off and extracted twice with dichloromethane, the combined organic phases are washed successively with 1N aqueous sodium hydroxide and then with saturated aqueous sodium chloride solution and are dried over sodium sulphate. Following evaporation of the solvent, the residue obtained is purified by chromatography on silica gel, eluting with a 98/2 mixture of dichloromethane and methanol.

This gives 0.28 g of pure product in the form of a white powder.

LC-MS: M+H=509
m.p. (° C.): 121-123° C.
$^1$H NMR (DMSO) δ (ppm): 8.1 (m, 3H); 7.95 (m, 2H); 7.6 (t, 1H); 7.3 (t, 2H); 7.20 (d, 1H); 6.80 (d, 1H); 6.60 (m, 1H); 4.40 (broad d, 2H); 3.1 (m, 2H); 2.8 (m, 2H); 1.75 (broad d, 2H); 1.55 (m, 1H); 1.4 (m, 2H); 1.1 (m, 2H).

EXAMPLE 5

Compound 52

2,2,2-Trifluoro-1-thiazol-4-ylethyl (+/−)-2-[6'-(4-fluorophenyl)-3,4,5,6-tetrahydro-2H-[1,2']bipyridinyl-4-yl]ethylcarbamate

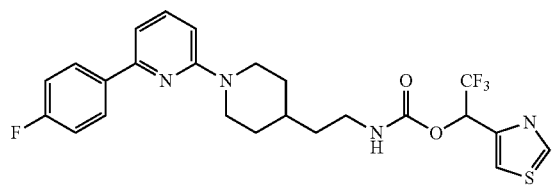

5.1. 2,2,2-Trifluoro-1-thiazol-4-ylethanol

The method described in Example 4 (step 4.5.) is followed. Starting from 1 g (8.84 mmol) of thiazole-4-carboxaldehyde, 0.10 ml (0.10 mmol) of a 1M solution of tetrabutylammonium fluoride in THF and 1.38 g (9.72 mmol) of trifluoromethyltrimethylsilane (TMS-CF$_3$), and after chromatography on silica gel, eluting with a 98/2 mixture of dichloromethane and methanol, gives 0.54 g of pure product in the form of a colourless oil.

5.2. 2,2,2-Trifluoro-1-thiazol-4-ylethyl (+/−)-2-[6'-(4-fluorophenyl)-3,4,5,6-tetrahydro-2H-[1,2']bipyridinyl-4-yl]ethylcarbamate The procedure described in Example 4 (step 4.6.) is followed. Starting from 0.183 g (1 mmol) of 4-nitrophenyl 2-[6'-(4-fluorophenyl)-3,4,5,6-tetrahydro-2H-[1,2']bipyridinyl-4-yl]ethylcarbamate, described in Example 4 (step 4.4.), 0.19 g (1.5 mmol) of N,N-diisopropylethylamine, 0.006 g (0.05 mmol) of N,N-dimethylaminopyridine and 0.51 g (1.1 mmol) of 2,2,2-trifluoro-1-thiazol-4-ylethanol, obtained in step 5.1., and after chromatography on silica gel, eluting with a 40/60 mixture of ethyl acetate and cyclohexane, followed by recrystallization from a mixture of diethyl ether and hexane, gives 0.240 g of pure product in the form of a white powder.

LC-MS: M+H=509
m.p. (° C.): 79-83° C.
$^1$H NMR (DMSO) δ (ppm): 9.2 (s, 1H); 8.1 (dd, 2H); 8 (s, 1H); 7.85 (broad t, 1H); 7.6 (dd, 1H); 7.35 (t, 2H); 7.15 (d, 1H); 6.80 (d, 1H); 6.45 (m, 1H); 4.40 (broad d, 2H); 3.15 (m, 2H); 2.8 (m, 2H); 1.75 (broad d, 2H); 1.55 (m, 1H); 1.4 (m, 2H); 1.1 (m, 2H).

EXAMPLE 6

Compound 55

2,2,2-Trifluoro-1-thiazol-5-ylethyl (+/−)-2-[6'-(4-fluorophenyl)-3,4,5,6-tetrahydro-2H-[1,2']bipyridinyl-4-yl]ethylcarbamate

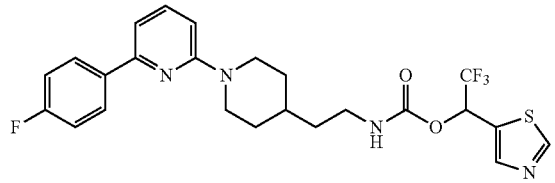 [SMILES: O=C(NCCC1CCN(c2cccc(-c3ccc(F)cc3)n2)CC1)OC(c1cncs1)C(F)(F)F]

6.1. 2,2,2-Trifluoro-1-thiazol-5-ylethanol

The method described in Example 4 (step 4.5.) is followed. Starting from 2 g (17.68 mmol) of thiazole-5-carboxaldehyde, 0.88 ml (0.88 mmol) of a 1M solution of tetrabutylammonium fluoride in THF and 2.765 g (19.44 mmol) of trifluoromethyltrimethylsilane (TMS-CF$_3$), and after chromatography on silica gel, eluting with a 98/2 mixture of dichloromethane and methanol, gives 2.23 g of pure product in the form of a colourless oil.

6.2. 2,2,2-Trifluoro-1-thiazol-5-ylethyl (+/−)-2-[6'-(4-fluorophenyl)-3,4,5,6-tetrahydro-2H-[1,2']bipyridinyl-4-yl]ethylcarbamate The procedure described in Example 4 (step 4,6.) is followed. Starting from 0.464 g (1 mmol) of 4-nitrophenyl 2-[6'-(4-fluorophenyl)-3,4,5,6-tetrahydro-2H-[0,2']bipyridinyl-4-yl]ethylcarbamate, described in Example 4 (step 4.4.), 0.19 g (1.5 mmol) of N,N-diisopropylethylamine, 0.006 g (0.05 mmol) of N,N-dimethylaminopyridine and 0.201 g (1.1 mmol) of 2,2,2-trifluoro-1-thiazol-5-ylethanol, obtained in step 6.1., and after chromatography on silica gel, eluting with a 98/2 mixture of dichloromethane and methanol, gives 0.240 g of pure product in the form of a gum.

LC-MS: M+H=509

$^1$H NMR (DMSO) δ (ppm): 9.3 (5, 1H); 8.2 (5, 1H); 8.1 (dd, 2H); 7.85 (broad t, 1H); 7.6 (dd, 1H); 7.25 (dd, 2H); 7.15 (d, 1H); 6.90 (m, 1H); 6.80 (d, 1H); 4.40 (broad d, 2H); 3.15 (m, 2H); 2.8 (m, 2H); 1.75 (broad d, 2H); 1.55 (m, 1H); 1.4 (m, 2H); 1.1 (m, 2H).

EXAMPLE 7

Compound 106

2,2,2-Trifluoro-1-thiazol-2-ylethyl (+/−)-2-[1-(6-chloroquinolin-2-yl)piperidin-4-yl]ethylcarbamate

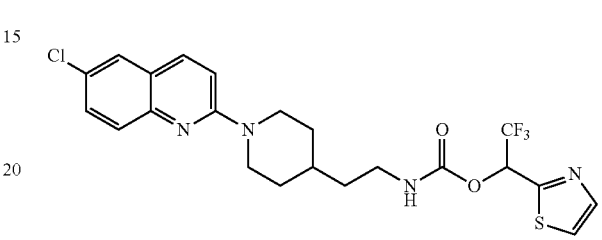

7.1. 2-[1-(6-Chloroquinolin-2-yl)piperidin-4-yl]ethyl methanesulphonate

A solution of 4 g (13.76 mmol) of 2-[1-(6-chloroquinolin-2-yl)piperidin-4-yl]ethanol (WO2004/099176), 3.55 g (27.51 mmol) of diisopropylethylamine and 0.84 g (6.88 mmol) of N,N-dimethylaminopyridine in 30 ml of dichloromethane, cooled to approximately 0° C., is admixed dropwise under an inert atmosphere with a solution of 2.36 g (20.63 mmol) of mesyl chloride in 3 ml of dichloromethane. Stirring is continued at 0° C. for two hours and then at ambient temperature for one hour.

Water is added to the reaction mixture, the aqueous phase is separated off and extracted a number of times with dichloromethane, the combined organic phases are washed with saturated aqueous sodium chloride solution and dried over sodium sulphate, and the filtrate is concentrated under reduced pressure.

This gives 5.1 g of product in the form of an oil, which is used as it is in the following step.

7.2. 2-[4-(2-Azidoethyl)piperidin-1-yl]-6-chloro-quinoline

A solution of 5 g (13.55 mmol) of 2-[1-(6-chloroquinolin-2-yl)piperidin-4-yl]ethyl methanesulphonate, prepared in step 7.1., and 1.76 g (27.11 mmol) of sodium azide in 30 ml of N,N-dimethylformamide is heated at reflux for 4 hours under an inert atmosphere.

Following return to ambient temperature, the reaction mixture is concentrated under reduced pressure. The residue is taken up in dichloromethane and water and the aqueous phase is separated off and extracted twice with dichloromethane, the combined organic phases are washed with saturated aqueous sodium chloride solution, and dried over sodium sulphate. Evaporation of the solvent gives 3.8 g of product in the form of an oil, which is used as it is in the following step.

7.3. 2-[1-(6-Chloroquinolin-2-yl)piperidin-4-yl]ethylamine

A solution of 3.5 g (11.08 mmol) of 2-[4-(2-azidoethyl) piperidin-1-yl]-6-chloroquinoline, obtained in step 7.2., in 100 ml of THF/water (1/1), is admixed in small portions at ambient temperature with 4.36 g (16.62 mmol) of triphenylphosphine. Stirring is continued at ambient temperature for ten hours.

The reaction mixture is concentrated under reduced pressure. Ethyl acetate is added, the aqueous phase is separated off and extracted three times with ethyl acetate, the combined organic phases are washed with saturated aqueous sodium chloride solution and dried over sodium sulphate, and the filtrate is concentrated under reduced pressure. Chromatography on silica gel, eluting with a 90/10/1 mixture of dichloromethane, methanol and 28% aqueous ammonia, gives 1.77 g of pure product in the form of an oil which crystallizes at ambient temperature.

m.p. (° C.): 68-70° C.

$^1$H NMR (CDCl$_3$) δ (ppm): 7.7 (d, 1H); 7.5 (m, 2H); 7.35 (m, 1H); 6.95 (d, 1H); 4.45 (broad d, 2H); 2.9 (broad td, 2H); 2.7 (t, 2H); 1.7 (m, 2H); 1.6-1.1 (m, 5H).

7.4 4-Nitrophenyl 2-[1-(6-chloroquinolin-2-yl)piperidin-4-yl]ethyl}carbamate The method described in Example 4 (step 4.4.) is followed. Starting from 5 g (17.25 mmol) of 2-[1-(6-chloroquinolin-2-yl)piperidin-4-yl]ethylamine, prepared in step 7.3., 3.825 g (18.98 mmol) of 4-nitrophenyl chloroformate, 4.46 g (34.51 mmol) of N,N-diisopropylethylamine and 0.105 g (0.86 mmol) of N,N-dimethylaminopyridine, and after trituration in a mixture of diisopropyl ether and hexane, gives 7.8 g of pure product in the form of a white powder.

m.p. (° C.): 80-84° C.

7.5. 2,2,2-Trifluoro-1-thiazol-2-ylethyl (+/−)-2-[1-(6-chloroquinolin-2-yl)piperidin-4-yl]ethylcarbamate The procedure described in Example 4 (step 4.6.) is followed. Starting from 0.455 g (1 mmol) of 4-nitrophenyl 2-[1-(6-chloroquinolin-2-yl)piperidin-4-yl]ethyl}carbamate obtained in step 7.4., 0.19 g (1.5 mmol) of N,N-diisopropylethylamine, 0.006 g (0.05 mmol) of N,N-dimethylaminopyridine and 0.201 g (1.1 mmol) of 2,2,2-trifluoro-1-thiazol-2-ylethanol, described in Example 5 (step 5.5.), and after chromatography on silica gel, eluting with a 98/2 mixture of dichloromethane and methanol, followed by recrystallization from a mixture of diethyl ether and hexane, gives 0.3 g of pure product in the form of a white powder.

LC-MS: M+H=499 m.p. (° C.): 114-116° C.

$^1$H NMR (DMSO) δ (ppm); 8.1 (t, 1H); 8 (m, 2H); 7.8 (s, 1H); 7.5 (m, 3H); 7.30 (d, 1H); 6.60 (m, 1H); 4.55 (broad d, 2H); 3.15 (m, 2H); 2.9 (m, 2H); 1.8 (broad d, 2H); 1.55 (m, 1H); 1.4 (m, 2H); 1.1 (m, 2H).

EXAMPLE 8

Compound 38

Thiazol-2-ylmethyl 2-[5'-(4-ethoxyphenyl)-3,4,5,6-tetrahydro-2H-[1,2']bipyridinyl-4-yl]ethylcarbamate

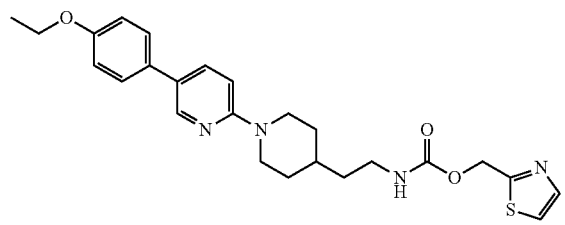 [SMILES: CCOc1ccc(-c2ccc(N3CCC(CCNC(=O)OCc4nccs4)CC3)nc2)cc1]

8.1. tert-Butyl 2-(5'-bromo-3,4,5,6-tetrahydro-2H-[1,2']bipyridinyl-4-yl)ethylcarbamate An autoclave is charged with 10.37 g (43.80 mmol) of 2,5-dibromopyridine, 10 g (43.80 mmol) of tert-butyl 2-piperidin-4-ylethylcarbamate and 6.05 g (43.8 mmol) of potassium carbonate. This initial charge is subsequently heated at 130° C. for 12 hours.

Following return to ambient temperature, the reaction mixture is taken up in chloroform and saturated aqueous sodium hydrogencarbonate solution. The aqueous phase is separated off and extracted twice with chloroform, the combined organic phases are washed with saturated aqueous sodium chloride solution and dried over sodium sulphate, and the filtrate is concentrated under reduced pressure.

Chromatography on silica gel, eluting with a 95/5 mixture of dichloromethane and methanol, gives 6.9 g of pure product in the form of a white powder.

m.p. (° C.): 108-110° C.

8.2. 2-(5'-Bromo-3,4,5,6-tetrahydro-2H-[1,2]bipyridinyl-4-yl)ethylamine

A solution of 6.9 g (17.95 mmol) of tert-butyl 2-(5'-bromo-3,4,5,6-tetrahydro-2H-[1,2]bipyridinyl-4-yl)ethylcarbamate obtained in step 8.1., in 100 ml of dichloromethane, cooled by an ice/water bath, is admixed slowly with 20.47 g (179.54 mmol) of trifluoroacetic acid. Stirring is continued at ambient temperature for 2 hours. The reaction mixture is poured into a mixture of ice-water and 28% aqueous ammonia. The mixture is decanted, the aqueous phase is extracted twice with dichloromethane, and the combined organic phases are washed with saturated aqueous sodium chloride solution, dried over sodium sulphate and concentrated under reduced pressure.

This gives 4.9 g of product in the form of an oil, which is used as it is in the following step.

8.3. Thiazol-2-ylmethyl 2-(5'-bromo-3,4,5,6-tetrahydro-2H-[1,2']bipyridinyl-4-yl)ethylcarbamate The procedure described in Example 1 (step 1.4.) is followed. Starting from 4.3 g (15.13 mmol) of 2-(5'-bromo-3,4,5,6-tetrahydro-2H-[1,2']bipyridinyl-4-yl)ethylamine, obtained in step 8.2., 4.66 g (16.64 mmol) of thiazol-2-ylmethyl (4-nitrophenyl)carbonate (EP486948A2), 2.93 g (2270 mmol) of N,N-diisopropylethylamine and 0.09 g (076 mmol) of N,N-dimethylamino-pyridine, and after chromatography on silica gel, eluting with a 20/80 mixture of ethyl acetate and cyclohexane, gives 2.6 g of pure product in the form of a white powder.

8.4. Thiazol-2-ylmethyl 2-[5'-(4-ethoxyphenyl)-3,4,5,6-tetrahydro-2H-[1,2']bipyridinyl-4-yl]ethylcarbamate Under an inert atmosphere, 0.425 g (1 mmol) of thiazol-2-ylmethyl 2-(5'-bromo-3,4,5,6-tetrahydro-2H-[1,2']bipyridinyl-4-yl)ethylcarbamate, obtained in step 8.3., 0.2 g (1.2 mmol) of 4-ethoxyphenylboronic acid and 0.977 g (3 mmol) of caesium carbonate in suspension in 5 ml of a 9/1 mixture of tetrahydrofuran and water are introduced. Subsequently 0.082 g (0.1 mmol) of $PdCl_2dppf.CH_2Cl_2$ is added. The mixture is subsequently heated at approximately 75° C. for 12 hours.

Following return to ambient temperature, the salts are separated off by filtration on Celite, and then the filtrate is taken up in ethyl acetate and water; the aqueous phase is separated off and extracted twice with ethyl acetate and the combined organic phases are washed with saturated aqueous sodium chloride solution and dried over sodium sulphate. Following evaporation of the solvent, the residue obtained is purified by chromatography on silica gel, eluting with a 98/2 mixture of dichloromethane and methanol. The solid obtained is subsequently recrystallized from isopropanol.

This gives 0.39 g of product in the form of a white powder.
LC-MS: M+H=467
m.p. (° C.): 157-159° C.
$^1$H NMR (DMSO) δ (ppm): 8.40 (s, 1H); 7.85 (d, 1H); 7.75 (m, 2H); 7.55 (d, 2H); 7.45 (t, 1H); 7 (d, 2H); 6.9 (d, 1H); 5.30 (s, 2H); 4.30 (broad d, 2H); 4.1 (q, 2H); 3.1 (m, 2H); 2.8 (t, 2H); 1.8 (d, 2H); 1.7 (m, 1H); 1.4 (m, 2H); 1.3 (t, 3H); 1.1 (m, 2H).

EXAMPLE 9

Compound 117

Thiazol-5-ylmethyl 2-[1-(6-fluoroquinolin-2-yl)piperidin-4-yl]ethylcarbamate

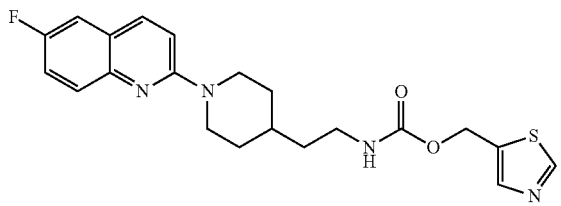 [SMILES: O=C(NCCC1CCN(c2ccc3cc(F)ccc3n2)CC1)OCc1cncs1]

9.1. tert-Butyl 4-[2-(4-nitrophenoxycarbonylamino)ethyl]piperidine-1-carboxylate The procedure described in Example 1 (step 1.4.) is followed. Starting from 5 g (21.90 mmol) of tert-butyl 4-(2-aminoethyl)piperidine-1-carboxylate, 4.63 g (23 mmol) of 4-nitrophenyl chloroformate, 5.66 g (43.80 mmol) of diisopropylethylamine and 0.134 g (1.09 mmol) of N,N-dimethylaminopyridine gives 8.6 g of product in the form of an oil which is used as it is in the following step.

9.2. tert-Butyl 4-[2-(thiazol-5-ylmethoxycarbonylamino)ethyl]piperidine-1-carboxylate The procedure described in Example 4 (step 4,6.) is followed. Starting from 8.6 g (21.86 mmol) of tert-butyl 4-[2-(4-nitrophenoxycarbonylamino)ethyl]-piperidine-1-carboxylate, obtained in step 9.1., 2.77 g (24.04 mmol) of thiazol-2-ylmethanol, 5.65 g (43.72 mmol) of N,N-diisopropylethylamine and 0.134 g (1.09 mmol) of N,N-dimethylaminopyridine gives 3.6 g of product in the form of an oil, which is used as it is in the following step.

9.3. Thiazol-5-ylmethyl 2-piperidin-4-ylethylcarbamate hydrochloride

A solution of 3.6 g (9.74 mmol) of tert-butyl 4-[2-(thiazol-5-ylmethoxycarbonylamino)ethyl]piperidine-1-carboxylate, obtained in step 9.2., in 97 ml of diethyl ether, cooled by an ice/water bath, is admixed slowly with 40 ml (160 mmol) of a 4N solution of hydrochloric acid in dioxane. Stirring is continued at ambient temperature for 12 hours.

Evaporation under reduced pressure gives 2.4 g of product in the form of the hydrochloride, which is used as it is in the following step.

9.4. Thiazol-5-ylmethyl 2-[1-(6-fluoroquinolin-2-yl)piperidin-4-yl]ethylcarbamate A sealed tube is charged with 0.09 g (0.39 mmol) of 2-bromo-6-fluoroquinoline, 0.1 g (0.33 mmol) of thiazol-5-ylmethyl 2-piperidin-4-ylethylcarbamate hydrochloride, obtained in step 9.3., and 0.2 ml (1.14 mol) of N,N-diisopropylethylamine. The system is subsequently heated at 100° C. for 12 hours.

Following return to ambient temperature, the reaction mixture is taken up in dichloromethane and saturated aqueous ammonium chloride solution. The aqueous phase is separated off and extracted twice with dichloromethane, the combined organic phases are washed with saturated aqueous sodium chloride solution and dried over sodium sulphate, and the filtrate is concentrated under reduced pressure.

Chromatography on silica gel, eluting with a 95/5 mixture of dichloromethane and methanol, gives 0.039 g of pure product in the form of a white powder.
LC-MS: M+H=415
m.p. (° C.): 100-102° C.
$^1$H NMR (DMSO) δ (ppm): 9.1 (s, 1H); 8 (d, 1H); 7.9 (s, 1H); 7.7 (m, 1H); 7.60 (dd, 1H); 7.5 (m, 1H); 7.30 (m, 2H); 5.3 (s, 2H); 4.50 (broad d, 2H); 3.10 (m, 2H); 2.85 (t, 2H); 1.9 (broad d, 2H); 1.60 (m, 1H); 1.4 (m, 2H); 1.1 (m, 2H).

Table 1 below illustrates the chemical structures and the physical properties of a number of compounds according to the invention. In this table:

- in the column "base or salt", "base" represents a compound in free base form, "$CF_3COOH$" represents a compound in trifluoroacetate form and "HCl" represents a compound in hydrochloride form;
- in the column "A", "1" corresponds to a —$CH_2$—, "2" corresponds to a —$CH_2$—$CH_2$—:
- all the compounds containing an asymmetric carbon are in racemic mixture form.

TABLE 1
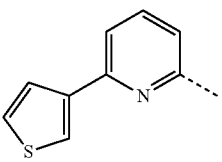
| No. | R₁ | m | n | A | R² | R³ | R⁴ | base or salt | m.p. (° C.) or M + H |
|---|---|---|---|---|---|---|---|---|---|
| 1. | 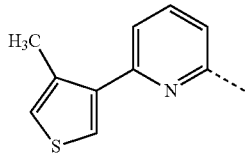 | 2 | 2 | 1 | H | H | thiazol-4-yl | CF₃COOH | 415 |
| 2. | | 2 | 2 | 2 | H | H | thiazol-4-yl | CF₃COOH | 429 |
| 3. | 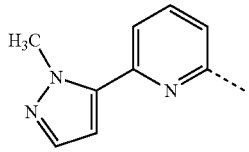 | 2 | 2 | 1 | H | H | thiazol-4-yl | CF₃COOH | 429 |
| 4. | | 2 | 2 | 2 | H | H | thiazol-4-yl | CF₃COOH | 443 |
| 5. | 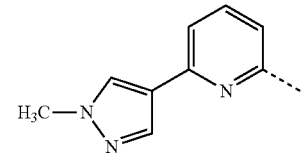 | 2 | 2 | 2 | H | H | thiazol-4-yl | CF₃COOH | 454 |
| 6. | 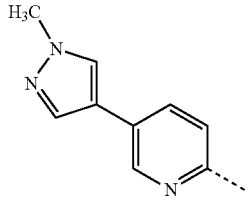 | 2 | 2 | 2 | H | H | thiazol-2-yl | HCl | 125-127° C. |
| 7. | | 2 | 2 | 1 | H | H | thiazol-4-yl | CF₃COOH | 413 |
| 8. | | 2 | 2 | 2 | H | H | thiazol-4-yl | base | 94-95° C. |
| 9. | 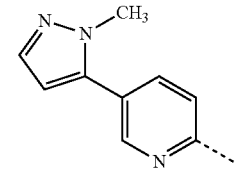 | 2 | 2 | 2 | H | H | thiazol-2-yl | base | 90° C. (dec.) |
| 10. | | 2 | 2 | 2 | H | H | thiazol-4-yl | base | 117-119° C. |
| 11. | (structure) | 2 | 2 | 2 | H | H | thiazol-4-yl | base | 153-155° C. |
| 12. | (structure) | 2 | 2 | 2 | H | H | thiazol-4-yl | base | 107-109° C. |

TABLE 1-continued

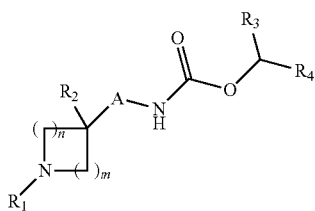

| No. | R₁ | m | n | A | R² | R³ | R⁴ | base or salt | m.p. (° C.) or M + H |
|---|---|---|---|---|---|---|---|---|---|
| 13. | | 2 | 2 | 2 | H | H | thiazol-2-yl | base | 132-534° C. |
| 14. | | 2 | 2 | 1 | H | H | thiazol-4-yl | CF₃COOH | 455 |
| 15. | (1-isobutyl-pyrazol-4-yl)-pyridin-2-yl | 2 | 2 | 2 | H | H | thiazol-4-yl | CF₃COOH | 469 |
| 16. | (1-isobutyl-pyrazol-4-yl)-pyridin-5-yl | 2 | 2 | 2 | H | H | thiazol-4-yl | base | 132-134° C. |
| 17. | | 2 | 2 | 1 | H | H | thiazol-4-yl | CF₃COOH | 428 |
| 18. | (3,5-dimethylisoxazol-4-yl)-pyridin-2-yl | 2 | 2 | 2 | H | H | thiazol-4-yl | CF₃COOH | 442 |
| 19. | | 2 | 2 | 1 | H | H | thiazol-4-yl | CF₃COOH | 413 |
| 20. | (4-methoxypyridin-3-yl)-pyridin-2-yl | 2 | 2 | 2 | H | H | thiazol-4-yl | CF₃COOH | 454 |
| 21. | | 2 | 2 | 2 | H | H | thiazol-2-yl | base | 124-126° C. |
| 22. | (5-fluoropyridin-3-yl)-pyridin-2-yl | 2 | 2 | 2 | H | H | thiazol-4-yl | base | 123-125° C. |
| 23. | (5-fluoropyridin-3-yl)-pyridin-3-yl | 2 | 2 | 2 | H | H | thiazol-4-yl | base | 133-135° C. |

TABLE 1-continued

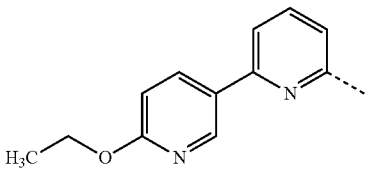

| No. | R₁ | m | n | A | R² | R³ | R⁴ | base or salt | m.p. (° C.) or M + H |
|---|---|---|---|---|---|---|---|---|---|
| 24. | 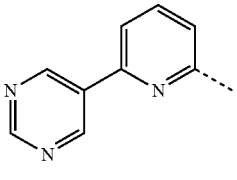 | 2 | 2 | 2 | H | H | thiazol-4-yl | CF₃COOH | 468 |
| 25. | 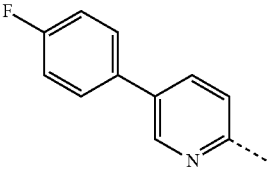 | 2 | 2 | 1 | H | H | thiazol-4-yl | CF₃COOH | 411 |
| 26. | 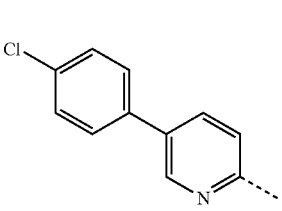 | 2 | 1 | 1 | H | H | thiazol-2-yl | base | 96-98° C. |
| 27. | | 2 | 1 | 1 | H | H | thiazol-4-yl | base | 106-108° C. |
| 28. | | 2 | 2 | 2 | H | H | thiazol-2-yl | base | 131-133° C. |
| 29. | | 2 | 2 | 2 | H | CF₃ | thiazol-2-yl | base | 132-134° C. |
| 30. | | 2 | 2 | 2 | H | H | thiazol-4-yl | base | 130-132° C. |
| 31. | | 2 | 2 | 2 | H | CF₃ | thiazol-4-yl | base | 120-122° C. |
| 32. | | 2 | 2 | 2 | H | H | 2-CH₃-thiazol-4-yl | base | 149-151° C. |
| 33. | | 2 | 2 | 2 | H | H | thiazol-5-yl | base | 100-102° C. |
| 34. | | 2 | 2 | 2 | H | CF₃ | thiazol-5-yl | base | 165-167° C. |
| 35. | 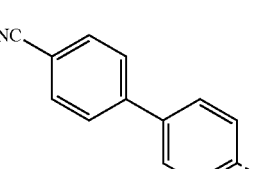 | 2 | 2 | 2 | H | H | thiazol-2-yl | base | 145-149° C. |
| 36. | 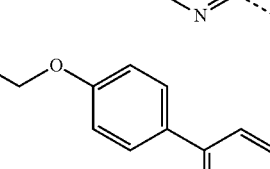 | 2 | 2 | 2 | H | H | thiazol-2-yl | base | 189-191° C. |
| 37. | | 2 | 2 | 2 | H | H | thiazol-5-yl | base | 147-149° C. |
| 38. | 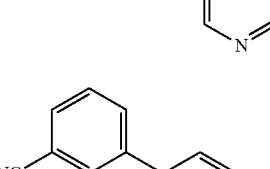 | 2 | 2 | 2 | H | H | thiazol-2-yl | base | 157-159° C. |
| 39. | | 2 | 2 | 2 | H | H | thiazol-4-yl | base | 160-162° C. |
| 40. | | 2 | 2 | 2 | H | H | thiazol-5-yl | base | 170-172° C. |
| 41. | 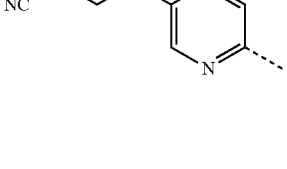 | 2 | 2 | 2 | H | H | thiazol-2-yl | base | 114-116° C. |

TABLE 1-continued

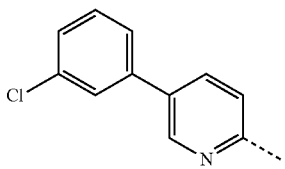

| No. | R₁ | m | n | A | R² | R³ | R⁴ | base or salt | m.p. (° C.) or M + H |
|---|---|---|---|---|---|---|---|---|---|
| 42. | 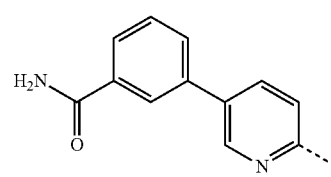 | 2 | 2 | 2 | H | H | thiazol-2-yl | base | 101-103° C. |
| 43. | 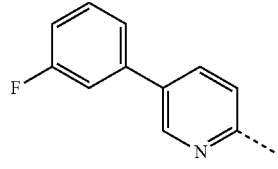 | 2 | 2 | 2 | H | H | thiazol-4-yl | base | 195-197° C. |
| 44. | 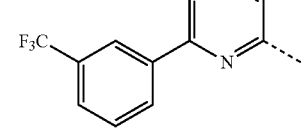 | 2 | 2 | 2 | H | H | thiazol-2-yl | base | 101-103° C. |
| 45. | 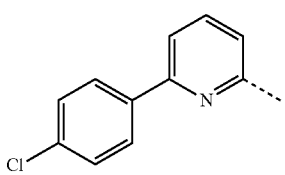 | 2 | 2 | 1 | H | H | thiazol-4-yl | CF₃COOH | 477 |
| 46. |  | 2 | 2 | 2 | H | H | thiazol-4-yl | CF₃COOH | 491 |
| 47. | 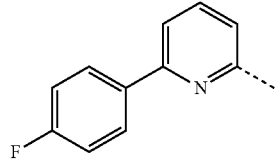 | 2 | 2 | 1 | H | H | thiazol-4-yl | CF₃COOH | 443 |
| 48. |  | 2 | 2 | 2 | H | H | thiazol-4-yl | CF₃COOH | 457 |
| 49. |  | 2 | 2 | 2 | H | H | thiazol-2-yl | base | 95-97° C. |
| 50. |  | 2 | 2 | 2 | H | CF₃ | thiazol-2-yl | base | 121-123° C. |
| 51. |  | 2 | 2 | 2 | H | H | thiazol-4-yl | base | 118-120° C. |
| 52. |  | 2 | 2 | 2 | H | CF₃ | thiazol-4-yl | base | 79-83° C. |
| 53. |  | 2 | 2 | 2 | H | H | 2-CH₃-thiazol-4-yl | base | 127-129° C. |
| 54. |  | 2 | 2 | 2 | H | H | thiazol-5-yl | base | 78-82° C. |
| 55. |  | 2 | 2 | 2 | H | CF₃ | thiazol-5-yl | base | 509 |
| 56. | 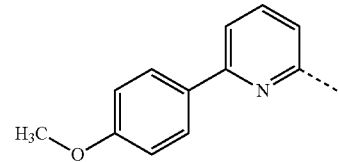 | 2 | 2 | 1 | H | H | thiazol-4-yl | CF₃COOH | 439 |
| 57. |  | 2 | 2 | 2 | H | H | thiazol-4-yl | CF₃COOH | 453 |

TABLE 1-continued
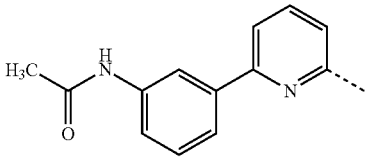
| No. | R₁ | m | n | A | R² | R³ | R⁴ | base or salt | m.p. (° C.) or M + H |
|---|---|---|---|---|---|---|---|---|---|
| 58. | 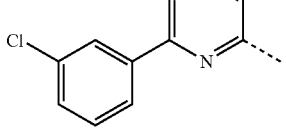 | 2 | 2 | 1 | H | H | thiazol-4-yl | CF₃COOH | 466 |
| 59. | | 2 | 2 | 2 | H | H | thiazol-4-yl | CF₃COOH | 480 |
| 60. | 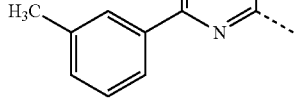 | 2 | 2 | 1 | H | H | thiazol-4-yl | CF₃COOH | 443 |
| 61. | | 2 | 2 | 2 | H | H | thiazol-4-yl | CF₃COOH | 457 |
| 62. | | 2 | 2 | 1 | H | H | thiazol-4-yl | CF₃COOH | 423 |
| 63. | | 2 | 2 | 2 | H | H | thiazol-4-yl | CF₃COOH | 437 |
| 64. | 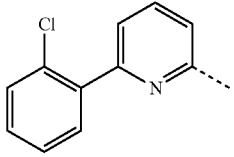 | 2 | 2 | 1 | H | H | thiazol-4-yl | CF₃COOH | 443 |
| 65. | 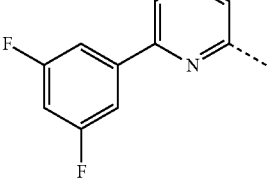 | 2 | 2 | 1 | H | H | thiazol-4-yl | CF₃COOH | 445 |
| 66. | | 2 | 2 | 2 | H | H | thiazol-4-yl | CF₃COOH | 459 |
| 67. | 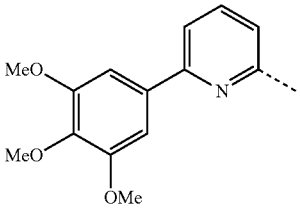 | 2 | 2 | 1 | H | H | thiazol-4-yl | CF₃COOH | 499 |

TABLE 1-continued

| No. | R₁ | m | n | A | R² | R³ | R⁴ | base or salt | m.p. (° C.) or M + H |
|---|---|---|---|---|---|---|---|---|---|
| 68. | 2,4-dimethoxyphenyl-pyridinyl | 2 | 2 | 2 | H | H | thiazol-4-yl | CF₃COOH | 483 |
| 69. | 4-isopropylphenyl-pyridinyl | 2 | 2 | 1 | H | H | thiazol-4-yl | CF₃COOH | 451 |
| 70. | 4-isopropylphenyl-pyridinyl | 2 | 2 | 2 | H | H | thiazol-4-yl | CF₃COOH | 465 |
| 71. | 3-isopropylphenyl-pyridinyl | 2 | 2 | 1 | H | H | thiazol-4-yl | CF₃COOH | 451 |
| 72. | 3-isopropylphenyl-pyridinyl | 2 | 2 | 2 | H | H | thiazol-4-yl | CF₃COOH | 465 |
| 73. | 4-cyclohexylphenyl-pyridinyl | 2 | 2 | 1 | H | H | thiazol-4-yl | CF₃COOH | 491 |
| 74. | 4-cyclohexylphenyl-pyridinyl | 2 | 2 | 2 | H | H | thiazol-4-yl | CF₃COOH | 505 |
| 75. | 3-(N,N-dimethylcarbamoyl)phenyl-pyridinyl | 2 | 2 | 1 | H | H | thiazol-4-yl | CF₃COOH | 480 |
| 76. | 3-(N,N-dimethylcarbamoyl)phenyl-pyridinyl | 2 | 2 | 2 | H | H | thiazol-4-yl | CF₃COOH | 494 |
| 77. | 4-sulfamoylphenyl-pyridinyl | 2 | 2 | 2 | H | H | thiazol-4-yl | CF₃COOH | 502 |

TABLE 1-continued

| No. | R₁ | m | n | A | R² | R³ | R⁴ | base or salt | m.p. (° C.) or M + H |
|---|---|---|---|---|---|---|---|---|---|
| 78. | | 2 | 2 | 1 | H | H | thiazol-4-yl | CF₃COOH | 452 |
| 79. | 4-carbamoylphenyl-pyridin-2-yl | 2 | 2 | 2 | H | H | thiazol-4-yl | CF₃COOH | 466 |
| 80. | | 2 | 2 | 1 | H | H | thiazol-4-yl | CF₃COOH | 452 |
| 81. | 3-carbamoylphenyl-pyridin-2-yl | 2 | 2 | 2 | H | H | thiazol-4-yl | CF₃COOH | 466 |
| 82. | | 2 | 2 | 1 | H | H | thiazol-4-yl | CF₃COOH | 480 |
| 83. | 3-(ethylcarbamoyl)phenyl-pyridin-2-yl | 2 | 2 | 2 | H | H | thiazol-4-yl | CF₃COOH | 494 |
| 84. | 3-(propylcarbamoyl)phenyl-pyridin-2-yl | 2 | 2 | 1 | H | H | thiazol-4-yl | CF₃COOH | 494 |
| 85. | 4-(methylsulfonamido)phenyl-pyridin-2-yl | 2 | 2 | 2 | H | H | thiazol-4-yl | CF₃COOH | 516 |
| 86. | | 2 | 2 | 1 | H | H | thiazol-4-yl | CF₃COOH | 482 |
| 87. | 4-(methoxysulfonamido)phenyl-pyridin-2-yl | 2 | 2 | 2 | H | H | thiazol-4-yl | CF₃COOH | 496 |
| 88. | 3-(pyrrolidin-1-yl)phenyl-pyridin-2-yl | 2 | 2 | 2 | H | H | thiazol-4-yl | CF₃COOH | 492 |

TABLE 1-continued

| No. | R₁ | m | n | A | R² | R³ | R⁴ | base or salt | m.p. (° C.) or M + H |
|---|---|---|---|---|---|---|---|---|---|
| 89. | morpholine-phenyl-pyridinyl | 2 | 2 | 1 | H | H | thiazol-4-yl | CF₃COOH | 494 |
| 90. | | 2 | 2 | 2 | H | H | thiazol-4-yl | CF₃COOH | 508 |
| 91. | ethoxy-phenyl-pyridinyl | 2 | 2 | 2 | H | H | thiazol-4-yl | CF₃COOH | 467 |
| 92. | cyclopropylmethoxy-phenyl-pyridinyl (para) | 2 | 2 | 2 | H | H | thiazol-4-yl | CF₃COOH | 493 |
| 93. | cyclopropylmethoxy-phenyl-pyridinyl (meta) | 2 | 2 | 1 | H | H | thiazol-4-yl | CF₃COOH | 479 |
| 94. | | 2 | 2 | 2 | H | H | thiazol-4-yl | CF₃COOH | 493 |
| 95. | NC-CH₂-phenyl-pyridinyl (para) | 2 | 2 | 1 | H | H | thiazol-4-yl | CF₃COOH | 448 |
| 96. | NC-CH₂-phenyl-pyridinyl (meta) | 2 | 2 | 1 | H | H | thiazol-4-yl | CF₃COOH | 448 |
| 97. | piperidine-sulfonyl-phenyl-pyridinyl | 2 | 2 | 1 | H | H | thiazol-4-yl | CF₃COOH | 556 |
| 98. | | 2 | 2 | 2 | H | H | thiazol-4-yl | CF₃COOH | 570 |

TABLE 1-continued

| No. | R₁ | m | n | A | R² | R³ | R⁴ | base or salt | m.p. (° C.) or M + H |
|---|---|---|---|---|---|---|---|---|---|
| 99. | (4-acetamidophenyl)pyridin-2-yl | 2 | 2 | 1 | H | H | thiazol-4-yl | CF₃COOH | 466 |
| 100 | (4-acetamidophenyl)pyridin-2-yl | 2 | 2 | 2 | H | H | thiazol-4-yl | CF₃COOH | 479 |
| 101 | 3-(methylsulfonyl)phenyl-pyridin-2-yl | 2 | 2 | 2 | H | H | thiazol-4-yl | CF₃COOH | 501 |
| 102 | 3-(ethylsulfonyl)phenyl-pyridin-2-yl | 2 | 2 | 1 | H | H | thiazol-4-yl | CF₃COOH | 501 |
| 103 | 3-(ethylsulfonyl)phenyl-pyridin-2-yl | 2 | 2 | 2 | H | H | thiazol-4-yl | CF₃COOH | 515 |
| 104 | 6-Cl-quinolin-2-yl | 2 | 2 | 2 | H | H | thiazol-2-yl | base | 121-123° C. |
| 105 | 6-Cl-quinolin-2-yl | 2 | 2 | 2 | H | H | 4-CF₃-thiazol-2-yl | base | 128-129° C. |
| 106 | 6-Cl-quinolin-2-yl | 2 | 2 | 2 | H | CF₃ | thiazol-2-yl | base | 114-116° C. |
| 107 | 6-Cl-quinolin-2-yl | 2 | 2 | 2 | H | CH₃ | thiazol-4-yl | base | 142-144° C. |
| 108 | 6-Cl-quinolin-2-yl | 2 | 2 | 2 | H | CF₃ | thiazol-4-yl | base | 111-113° C. |
| 109 | 6-Cl-quinolin-2-yl | 2 | 2 | 2 | H | H | thiazol-4-yl | base | 126-128° C. |
| 110 | 6-Cl-quinolin-2-yl | 2 | 2 | 2 | H | H | 2-CH₃-thiazol-4-yl | base | 142-144° C. |
| 111 | 6-Cl-quinolin-2-yl | 2 | 2 | 2 | H | H | 2-CF₃-thiazol-4-yl | base | 148-150° C. |
| 112 | 6-Cl-quinolin-2-yl | 2 | 2 | 2 | H | H | 2-Cl-thiazol-4-yl | base | 130-132° C. |
| 113 | 6-Cl-quinolin-2-yl | 2 | 2 | 2 | H | H | 2-(pyridin-3-yl)-thiazol-4-yl | base | 152-154° C. |
| 114 | 6-Cl-quinolin-2-yl | 2 | 2 | 2 | H | H | 2-(pyridin-4-yl)-thiazol-5-yl | base | 155-157° C. |
| 115 | 6-Cl-quinolin-2-yl | 2 | 2 | 2 | H | H | thiazol-5-yl | base | 132-134° C. |
| 116 | 6-Cl-quinolin-2-yl | 2 | 2 | 2 | H | CF₃ | thiazol-5-yl | base | 131-133° C. |
| 117 | 6-F-quinolin-2-yl | 2 | 2 | 2 | H | H | thiazol-5-yl | base | 100-102° C. |
| 118 | 7-F-quinolin-2-yl | 2 | 2 | 2 | H | H | thiazol-5-yl | base | 115-117° C. |
| 119 | 6-(naphthalen-1-yl)pyridin-2-yl | 2 | 2 | 1 | H | H | thiazol-4-yl | CF₃COOH | 459 |
| 120 | 6-(naphthalen-1-yl)pyridin-2-yl | 2 | 2 | 2 | H | H | thiazol-4-yl | CF₃COOH | 473 |

TABLE 1-continued

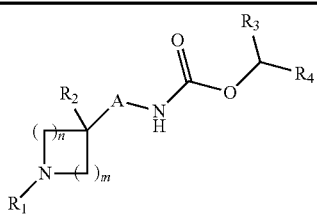

| No. | R₁ | m | n | A | R² | R³ | R⁴ | base or salt | m.p. (° C.) or M + H |
|---|---|---|---|---|---|---|---|---|---|
| 121 | (2-naphthyl-pyridyl) | 2 | 2 | 1 | H | H | thiazol-4-yl | CF₃COOH | 459 |
| 122 | | 2 | 2 | 2 | H | H | thiazol-4-yl | CF₃COOH | 473 |
| 123 | (quinolin-4-yl-pyridyl) | 2 | 2 | 1 | H | H | thiazol-4-yl | CF₃COOH | 460 |
| 124 | | 2 | 2 | 2 | H | H | thiazol-4-yl | CF₃COOH | 474 |
| 125 | (quinolin-6-yl-pyridyl) | 2 | 2 | 1 | H | H | thiazol-4-yl | CF₃COOH | 460 |
| 126 | | 2 | 2 | 2 | H | H | thiazol-4-yl | CF₃COOH | 474 |
| 127 | (isoquinolin-4-yl-pyridyl) | 2 | 2 | 1 | H | H | thiazol-4-yl | CF₃COOH | 460 |
| 128 | | 2 | 2 | 2 | H | H | thiazol-4-yl | CF₃COOH | 474 |
| 129 | (isoquinolin-5-yl-pyridyl) | 2 | 2 | 1 | H | H | thiazol-4-yl | CF₃COOH | 460 |
| 130 | | 2 | 2 | 2 | H | H | thiazol-4-yl | CF₃COOH | 474 |
| 131 | (4-F-phenyl-pyridyl) | 2 | 2 | 2 | H | H | 2-CONH₂-thiazol-4-yl | base | 230-232° C. |
| 132 | | 2 | 2 | 2 | H | H | 2-CONHCH₃-thiazol-4-yl | base | 184-186° C. |
| 133 | | 2 | 2 | 2 | H | H | 4-CONH₂-thiazol-2-yl | base | 199-201° C. |
| 134 | | 2 | 2 | 2 | H | H | 4-CONHCH₃-thiazol-2-yl | base | 177-178° C. |

LC-MS methods (M+H):
Acetonitrile+0.5% trifluoroacetic acid/H₂O+0.05% trifluoroacetic acid
Columns: Waters Xbridge C18 4 or YMC Jsphere 33*2
Flow rate: 1 ml/min The compounds of the invention were subjected to pharmacological tests allowing determination of their inhibitory effect on the enzyme FAAH (Fatty Acid Amide Hydrolase).

The inhibitory activity was demonstrated in a radioenzymatic assay based on measuring the product of hydrolysis of anandamide [1-³H ethanolamine] by FAAH (*Life Sciences* (1995), 56, 1999-2005 and *Journal of Biochemical and Biophysical Methods* (2004), 60(2), 171-177). Accordingly, mouse brains (minus the cerebellum) are removed and stored at −80° C. Membrane homogenates are prepared at the time of use by homogenizing the tissues using a Precellys® apparatus in the reaction buffer (10 mM Tris-HCl pH=8, 150 mM NaCl and 1 mM ethylenediaminetetraacetic acid (EDTA)). The enzymatic reaction is conducted in 96-well Multiscreen filter plates, in a final volume of 70 μl. Reaction buffer supplemented with bovine serum albumin without fatty acids (BSA, 1 mg/ml) is used for the enzymatic reaction, the dilution of the compounds and of anandamide [1-$^3$H ethanolamine]. Added in succession to the wells are the reaction buffer containing the BSA (43 µl/well), the diluted test compounds at different concentrations (7 µl/well containing 1% DMSO) and the membrane preparation (10 µl/well or 200 of tissue per assay). After the compounds have been pre-incubated with the enzyme at 25° C. for 20 minutes, the reaction is initiated by the addition of anandamide [1-$^3$H ethanolamine] (specific activity of 15-20 Ci/mmol) diluted with cold anandamide (10 µl/well, final concentration of 10 µM, 0.01 per assay). After 20 minutes of incubation at 25° C., the enzymatic reaction is halted by addition of a 5M active carbon solution prepared in a 1.5M NaCl and 0.5M HCl buffer (50 µl/well). The mixture is stirred for 10 minutes and then the aqueous phase containing the ethanolamine [1-$^3$H] is recovered by filtration under vacuum and counted by liquid scintillation.

Under these conditions the most active compounds of the invention exhibit $IC_{50}$ values (concentration inhibiting by 50% the control enzymatic activity of FAAH) of between 0.001 and 1 µM; for example compounds 28 and 30 have $IC_{50}$ values of 0.003 and 0.007 µM respectively.

It is therefore apparent that the compounds according to the invention have an inhibitory activity on FAAH enzyme.

The in vivo activity of the compounds of the invention was evaluated in an analgesia test.

Accordingly, intraperitoneal (i.p.) administration of PBQ (phenylbenzoquinone, 2 mg/kg in a 0.9% sodium chloride solution containing 5% of ethanol) to male OF 1 mice weighing 25 to 30 g causes abdominal stretches, on average 30 twists or contractions during the period from 5 to 15 minutes after injection. The test compounds are administered orally (p.o.) or intraperitoneally (i.p.) in suspension in Tween 80 at 0.5%, 60 minutes or 120 minutes before the administration of PBQ. Under these conditions the most potent compounds of the invention reduce by 35% to 80% the number of stretches induced by PBQ, within a dose range of between 1 and 30 mg/kg.

For example, compounds 28 and 30 of the table reduce by 33% and 80%, respectively, the number of stretches induced by PBQ, at a dose of 30 mg/kg p.o. at 120 minutes.

The enzyme FAAH (*Chemistry and Physics of Lipids*, (2000), 108, 107-121) catalyses the hydrolysis of endogenous derivatives of amides and of esters of various fatty acids such as N-arachidonoylethanolamine (anandamide), N-palmitoylethanolamine, N-oleoylethanolamine, oleamide or 2-arachidonoylglycerol. These derivatives exert various pharmacological activities by interacting, inter alia, with cannabinoid and vanilloid receptors. The compounds of the invention block this degradation pathway and increase the tissue level of these endogenous substances. They can be used in this respect in the prevention and treatment of pathologies involving endogenous cannabinoids and/or any other substrates metabolized by the FAAH enzyme. Mention may be made, for example, of the following diseases and conditions: pain, especially acute or chronic pain of neurogenic type: migraine, neuropathic pain, including forms associated with the herpes virus and with diabetes and with chemotherapy, acute or chronic pain associated with inflammatory diseases: arthritis, rheumatoid arthritis, osteoarthritis, spondylitis, gout, vasculitis. Crohn's disease, irritable bowel syndrome, acute or chronic peripheral pain, dizziness, vomiting, nausea, especially subsequent to chemotherapy, eating disorders, especially anorexia and cachexia of various kinds, neurological and psychiatric pathologies: shaking, dyskinesia, dystonia, spasticity, obsessive-compulsive behaviours, Tourette's syndrome, all forms of depression and anxiety of any kind and cause, mood disorders, psychoses, acute and chronic neurodegenerative diseases: Parkinson's disease, Alzheimer's disease, senile dementia, Huntington's chorea, lesions associated with cerebral ischaemia and with cranial and medullary trauma, epilepsy, sleep disorders, including sleep apnoea, cardiovascular diseases, especially hypertension, cardiac arrhythmias, arteriosclerosis, heart attack, cardiac ischaemia, renal ischaemia, cancers: benign skin tumours, papillomas and brain tumours, prostate tumours, brain tumours (glioblastomas, medulloepitheliomas, medulloblastomas, neuroblastomas, tumours of embryonic origin, astrocytomas, astroblastomas, ependyomas, oligodendrogliomas, plexus tumour, neuroepitheliomas, epiphysial tumour, ependymoblastomas, malignant meningiomas, sarcomatoses, malignant melanomas, schwannomas), disorders of the immune system, especially autoimmune diseases: psoriasis, lupus erythematosis, diseases of the connective tissue or collagen diseases. Sjögren's syndrome, ankylosing spondylarthritis, undifferentiated spondylarthritis. Behcet's disease, haemolytic autoimmune anaemias, multiple sclerosis, amyotrophic lateral sclerosis, amyloses, transplant rejection, diseases affecting the plasmocytic line, allergic diseases: immediate or delayed-onset hypersensitivity, allergic rhinitis or conjunctivitis, contact dermatitis, infectious parasitic, viral or bacterial diseases: AIDS, meningitis, inflammatory diseases, especially diseases of the joints: arthritis, rheumatoid arthritis, osteoarthritis, spondylitis, gout, vasculitis. Crohn's disease, irritable bowel syndrome, osteoporosis, ocular conditions: ocular hypertension, glaucoma, pulmonary conditions: diseases of the respiratory tract, bronchospasms, coughing, asthma, chronic bronchitis, chronic obstruction of the respiratory tract, emphysema, gastrointestinal diseases: irritable bowel syndrome, intestinal inflammatory disorders, ulcers, diarrhoea, urinary incontinence and bladder inflammation.

The use of the compounds according to the invention, in the form of the base, an addition salt with an acid, a hydrate or pharmaceutically acceptable solvate, for preparing a medicinal product intended for treating the abovementioned pathologies forms an integral part of the invention.

The invention also provides medicinal products which comprise a compound of formula (I), or an addition salt with an acid, or else a hydrate or a pharmaceutically acceptable solvate of the compound of formula (I). These medicinal products are employed in therapy, especially in the treatment of the abovementioned pathologies.

According to another of its aspects the present invention provides pharmaceutical compositions comprising as active principle at least one compound according to the invention. These pharmaceutical compositions include an effective dose of a compound according to the invention, or an addition salt with an acid, or a hydrate, or a pharmaceutically acceptable solvate of said compound, and, optionally, one or more pharmaceutically acceptable excipients.

The said excipients are selected, according to the pharmaceutical form and the desired mode of administration, from the customary excipients which are known to a person skilled in the art.

In the pharmaceutical compositions of the present invention for oral, sublingual, subcutaneous, intramuscular, intravenous, topical, local, intrathecal, intranasal, transdermal, pulmonary, ocular or rectal administration, the active principle of formula (I) above, or its addition salt with an acid, solvate or hydrate, where appropriate, may be administered in a unit-dose administration form, in a mixture with conventional pharmaceutical excipients, to animals and to humans for the prophylaxis or treatment of the above disorders or diseases.

The unit-dose administration forms which are appropriate include oral forms such as tablets, soft or hard gelatin capsules, powders, granules, chewing gums and oral solutions or suspensions, forms for sublingual, buccal, intratracheal, intraocular and intranasal administration, and for administration by inhalation, forms for subcutaneous, intramuscular or intravenous administration, and forms for rectal or vaginal administration. For topical application the compounds according to the invention may be used in creams, ointments or lotions.

By way of example, a unit-dose administration form of a compound according to the invention in tablet form may comprise the following components:

| | |
|---|---:|
| Compound according to the invention | 50.0 mg |
| Mannitol | 223.75 mg |
| Sodium croscaramellose | 6.0 mg |
| Corn starch | 15.0 mg |
| Hydroxypropyl-methylcellulose | 2.25 mg |
| Magnesium stearate | 3.0 mg |

The said unit-dose forms contain a dose permitting daily administration of 0.01 to 20 mg of active principle per kg of body weight, depending on the pharmaceutical form.

There may be particular cases in which higher or lower doses are appropriate; such doses also belong to the invention. In accordance with customary practice, the dosage appropriate for each patient is determined by the doctor according to the mode of administration, the weight and the response of the said patient.

According to another of its aspects the invention likewise provides a method of treating the pathologies indicated above, which comprises administering an effective dose of a compound according to the invention, one of its addition salts with a pharmaceutically acceptable acid, a solvate or a hydrate of the said compound.

The invention claimed is:

1. Compound of the formula (I)

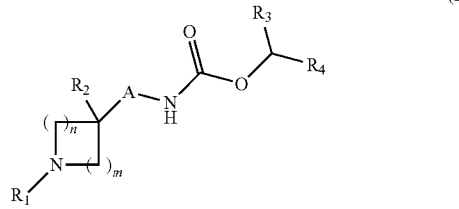

(I)

in which $R_2$ represents a hydrogen or fluorine atom, a hydroxyl, cyano, trifluoromethyl, $C_{1-6}$ alkyl or $C_{1-6}$ alkoxy group or a group $NR_8R_9$;

n represents an integer 2 and m represents an integer 2;

A represents a covalent bond or a $C_{1-8}$ alkylene group;

$R_1$ represents a group $R_5$ which is optionally substituted by one or more groups $R_6$ and/or $R_7$;

$R_5$ represents a pyridinyl group;

$R_6$ represents a halogen atom, a cyano, —CH$_2$CN, nitro, hydroxyl, $C_{1-6}$ alkyl, $C_{1-6}$ alkoxy, $C_{1-6}$ thioalkyl, $C_{1-6}$ haloalkyl, $C_{1-6}$ haloalkoxy, $C_{1-6}$ halothioalkyl, $C_{3-7}$ cycloalkyl, $C_{3-7}$ cycloalkyl-$C_{1-3}$ alkylene or $C_{3-7}$ cycloalkyl-$C_{1-3}$ alkylene-O— group, or a group $NR_8R_9$, $NR_8COR_9$, $NR_8CO_2R_9$, $NR_8SO_2R_9$, $NR_8SO_2NR_8R_9$, $COR_8$, $CONR_8R_9$, $SO_2R_8$, $SO_2NR_8R_9$ or —O—(C$_{1-3}$-alkylene)-O—;

$R_7$ represents a group selected from a thienyl, isoxazolyl, pyrazolyl, phenyl, pyridinyl, pyrimidinyl, naphthalenyl, quinolinyl or isoquinolinyl, the group or groups $R_7$ being able to be substituted by one or more groups $R_6$ which are identical or different from one another;

$R_3$ represents a hydrogen or fluorine atom, a $C_{1-6}$ alkyl group or a trifluoromethyl group;

$R_4$ represents a thiazole which is optionally substituted by one or more substituents selected from a $C_{1-6}$ alkyl and $CONR_8R_9$;

$R_8$ and $R_9$ represent independently of one another a hydrogen atom or a $C_{1-6}$ alkyl group, or form, with the atom or atoms bearing them, in the case of $NR_8R_9$, a ring selected from azetidine, pyrrolidine, piperidine, morpholine, thiomorpholine, azepine, oxazepine or piperazine ring, this ring being optionally substituted by a $C_{1-6}$ alkyl or benzyl group;

in the case of $NR_8COR_9$, a lactam ring; in the case of $NR_8CO_2R_9$, an oxazolidinone, oxazinone or oxazepinone ring; in the case of $NR_8SO_2R_9$, a sultam ring; in the case of $NR_8SO_2NR_8R_9$, a thiazolidine dioxide or thiadiazinane dioxide ring;

in the form of the base or an addition salt with an acid.

2. Compound of formula (I) according to claim 1, characterized in that $R_2$ represents
a hydrogen atom;
in the form of the base or an addition salt with an acid.

3. Compound of formula (I) according to claim 1, wherein A represents a $C_{1-8}$ alkylene group; in the form of the base or an addition salt with an acid.

4. Compound of formula (I) according to claim 1, wherein $R_1$ represents
a group $R_5$ which is optionally substituted by one or more groups $R_6$ and/or $R_7$;
$R_6$ represents a halogen atom, a cyano, —CH$_2$CN, $C_{1-6}$ alkyl, $C_{1-6}$ alkoxy, $C_{1-6}$ haloalkyl, $C_{3-7}$ cycloalkyl or $C_{3-7}$ cycloalkyl-$C_{1-3}$ alkylene-O— group, or a group $NR_8R_9$, $NR_8COR_9$, $NR_8CO_2R_9$, $NR_8SO_2R_9$, $CONR_8R_9$, $SO_2R_8$ or $SO_2NR_8R_9$;
$R_8$ and $R_9$ represent independently of one another a hydrogen atom or a $C_{1-6}$ alkyl group, or form with the atom or atoms bearing them a ring selected from pyrrolidine, piperidine and morpholine rings; in the form of the base or an addition salt with an acid.

5. Compound of formula (I) according to claim 1, wherein $R_3$ represents a hydrogen atom, a $C_{1-6}$ alkyl group or a trifluoromethyl group; in the form of the base or an addition salt with an acid.

6. Compound of formula (I) according to claim 1, wherein $R_4$ represents a thiazole which is optionally substituted by one or more substituents selected from $C_{1-6}$ alkyl and $CONR_8R_9$ group; $R_8$ and $R_9$ represent independently of one another a hydrogen atom or a $C_{1-6}$ alkyl group;
in the form of the base or an addition salt with an acid.

7. Compound of formula (I) according to claim 1, in the form of the base or an addition salt with a pharmaceutically acceptable acid, for use thereof as a medicinal product.

8. A compound selected from the group consisting of thiazol-2-ylmethyl{1-[5-(4-fluorophenyl)pyridin-2-yl]pyrrolidin-3-yl)}methylcarbamate and thiazol-4-ylmethyl {1-[5-(4-fluorophenyl)pyridin-2-yl]pyrrolidin-3-yl)}methylcarbamate; in the form of the base or an addition salt with an acid.

9. Process for preparing a compound of formula (I) according to claim 1, comprising the step of
reacting an amine of general formula (II)

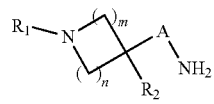
(II)

in which A, $R_1$, $R_2$, m and n are as defined in the general formula (I) according to claim 1, with a carbonate of general formula (III)

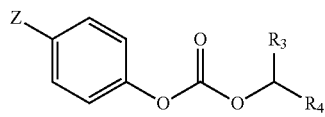
(III)

in which Z represents a hydrogen atom or a nitro group and $R_3$ and $R_4$ are as defined in the general formula (I) according to claim 1,
in the presence of a base, in a solvent at a temperature between the ambient temperature and the reflux temperature of the solvent.

10. Process for preparing a compound of formula (I) according to claim 1, comprising the step of
reacting an amine of general formula (II)

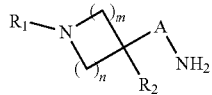
(II)

in which A, $R_1$, $R_2$, m and n are as defined in the general formula (I) according to claim 1, with phenyl or 4-nitrophenyl chloroformate,
in the presence of a base, in a solvent at a temperature between 0° C. and the ambient temperature, to give the carbamate derivative of general formula (IV)

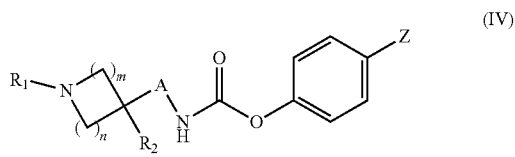
(IV)

in which A, $R_1$, $R_2$, m and n are as defined in the general formula (I) according to claim 1, and Z represents a hydrogen atom or a nitro group;
then converting the carbamate derivative of general formula (IV) thus obtained into a compound of general formula (I), by the action of an alcohol of general formula $HOCHR_3R_4$ (Ina), in which $R_3$ and $R_4$ are as defined in general formula (I) according to claim 1,
in the presence of a base, in a solvent at a temperature between the ambient temperature and the reflux temperature of the solvent.

11. Pharmaceutical composition comprising at least one compound of formula (I) according to claim 1, in the form of the base or an addition salt with a pharmaceutically acceptable acid, and, optionally, one or more pharmaceutically acceptable excipients.

* * * * *